(12) United States Patent
Orlowski

(10) Patent No.: US 9,981,058 B2
(45) Date of Patent: May 29, 2018

(54) BALLOON SURFACE COATING

(75) Inventor: Michael Orlowski, Bonn (DE)

(73) Assignee: CARDIONOVUM Sp.z.o.o., Warsaw (PL)

( * ) Notice: Subject to any disclaimer, the term of this patent is extended or adjusted under 35 U.S.C. 154(b) by 0 days. days.

(21) Appl. No.: 13/978,203

(22) PCT Filed: Jul. 4, 2012

(86) PCT No.: PCT/EP2012/062995
§ 371 (c)(1),
(2), (4) Date: Jul. 3, 2013

(87) PCT Pub. No.: WO2013/045126
PCT Pub. Date: Apr. 4, 2013

(65) Prior Publication Data
US 2014/0276404 A1 Sep. 18, 2014

(30) Foreign Application Priority Data
Sep. 29, 2011 (WO) ................. PCT/EP2011/004863

(51) Int. Cl.
| A61M 31/00 | (2006.01) |
| A61L 26/00 | (2006.01) |
| A61L 29/08 | (2006.01) |
| A61L 29/16 | (2006.01) |

(52) U.S. Cl.
CPC ......... *A61L 26/0014* (2013.01); *A61L 29/085* (2013.01); *A61L 29/16* (2013.01); *A61L 2300/602* (2013.01)

(58) Field of Classification Search
CPC .......... A61M 2025/105; A61L 26/0014; A61L 29/085; A61L 29/16; A61L 2300/602

USPC ..................................................... 604/103.02
See application file for complete search history.

(56) References Cited

U.S. PATENT DOCUMENTS

| 5,622,714 A | * | 4/1997 | Dietl ............................. 424/450 |
| 6,388,112 B1 | * | 5/2002 | Anevski ............... A61K 31/337 554/191 |
| 6,726,930 B1 | * | 4/2004 | Baichwal ............. A61K 9/1611 424/464 |
| 6,749,554 B1 | * | 6/2004 | Snow .................... A61L 29/085 600/3 |
| 2008/0255508 A1 | * | 10/2008 | Wang ....................... 604/103.02 |
| 2008/0255510 A1 | | 10/2008 | Wang |
| 2010/0010470 A1 | * | 1/2010 | Bates .......................... 604/509 |

(Continued)

OTHER PUBLICATIONS

BASF Pharma Ingredients & Services, "Kollicoat IR", Feb. 2010, pp. 3 and 4.*

(Continued)

*Primary Examiner* — Kevin C Sirmons
*Assistant Examiner* — Leah Swanson
(74) *Attorney, Agent, or Firm* — Amin, Turocy & Watson LLP

(57) ABSTRACT

The present invention is directed to catheter balloons and balloon catheters with such catheter balloons coated with at least one layer containing at least one antiproliferative, immunosuppressive, anti-angiogenic, anti-inflammatory, anti-restenotic and/or anti-thrombotic agent and a top coat consisting of a polyvinyl alcohol—polyethylene glycol graft copolymer as well as the use of these balloon catheters for the prevention of restenosis.

11 Claims, 4 Drawing Sheets

(56) References Cited

U.S. PATENT DOCUMENTS

2010/0076401 A1* 3/2010 Von Oepen ............. A61F 2/958
                                                     604/509
2010/0209472 A1* 8/2010 Wang ........................... 424/423

OTHER PUBLICATIONS

International Search Report for PCT/EP2012/062995 dated Jan. 28, 2013.
Written Opinion for PCT/EP2012/062995 dated Jan. 28, 2013.

* cited by examiner

BALLOON SURFACE COATING

The present invention is directed to catheter balloons and balloon catheters with such catheter balloons coated with at least one layer containing at least one antiproliferative, immunosuppressive, anti-angiogenic, anti-inflammatory, anti-restenotic and/or anti-thrombotic agent and a top coat consisting of a polyvinyl alcohol—polyethylene glycol graft copolymer as well as the use of these balloon catheters for the prevention of restenoses.

Implantation of vessel grafts such as stents has become a well-established surgical intervention for the treatment of stenosis. In this context, so-called restenosis (recurrent stenosis), i.e. the reocclusion of the vessel is a frequently occurring complication. There's no exact definition of the term restenosis to be found in literature. The most frequently used morphological definition of restenosis defines restenosis as a reduction of the vessel diameter to less than 50% of the normal value subsequent to successful PTA (percutaneous transluminal angioplasty). Said definition describes an empirically determined value and its hemodynamic meaning and association with clinical symptoms lack scientific background. In practice, clinical deterioration in a patient is often considered a sign for the occurrence of restenosis in the previously treated vessel section.

In PCTA the occluded part is enlarged for a short time of 1 to 3 minutes by means of an inflatable balloon at the catheter tip, if necessary repeated for more than two times. Herein the vessels must be overstretched in such a way that the occlusion is removed. From this procedure micro-lesions result in the vascular wall reaching up to the adventitia. After removing the catheter the injured vessel segment is left alone so that considerably high performance is required for the healing process, in dependence of the inflicted lesion grade resulting from the duration, the repetitions and the grade of overstretching. This is reflected in the high re-occlusion rate after PCTA.

Endoprosthesis or stents supporting or keeping vessels open once they have been implanted into injured blood vessels, e.g. in the case of stenosis, dissections, etc. have been long-known in minimal-invasive interventional medicine. Usually, they are produced from metals such as stainless steel or nitinol. A large number of such metal stents is known and well established in practice. Due to their metal structure and carrying capacity, such metal stents are supposed to ensure that the vessels remain open after implantation and that the blood flow through the vessels is permanently guaranteed.

In stent implantation a balloon catheter is used as a transport and implant aid. If the stent is unalterably stuck in the correct position the balloon is deflated again and can be removed. Also herein overstretching of the vascular wall occurs during dilatation. However, use of PTCA alone shows clear advantages in comparison to the stent, not least because there is at no time after treatment a foreign body in the organism, resulting in additional stress or being the starting point of after-effects, such as restenosis and thrombosis such as late in stent thrombosis. Therefore there exist linkages to work done in the late 80s concerning an active substance releasing balloon catheter.

The problem of late thromboses caused by drug eluting stents like paclitaxel eluting stents have been described as serious problem which can cause death of the patient. In comparison to drug eluting stents which release the drug over a certain period of time, drug coated catheter balloons need to immediately release the drug since dilatation of a catheter balloon cannot take longer than 60 seconds in order to avoid any harm to the patient and might be repeated for two or three times. However even repeating the dilatation in order to obtain three or four or five minutes of over-all dilatation time is still a short time release of the drug in comparison with stents which release the drug over days, weeks or months.

To avoid such problems, a so-called "biological stenting" may be performed using only a coated catheter balloon without any stent, i.e. the vessels are dilated at a constricted site by the dilatation of a coated catheter balloon, wherein, while the catheter balloon is dilated for a short period of time, a sufficient amount of pharmacological agent is transferred to the vessel wall to avoid re-constriction or re-occlusion of the vessel due to the dilatation of the vessel and the delivery of active agents. Furthermore, we as well as other research groups have found that the hitherto measured paclitaxel concentrations in porcine coronary artery after treatment with paclitaxel coated catheter balloons without any excipient (pure drug coating) were not effective in exerting a therapeutic effect on the inhibition of restenosis. The authors of a publication in Circulation 2004, Vol. 110, 810-814 demonstrated that catheter balloons coated with pure Paclitaxel did not show any therapeutic effect. A therapeutic effect was only achieved when the Paclitaxel was combined with the contrast agent solution ULTRAVIST® (Iopromid). ULTRAVIST® (Iopromid) is a solution of the contrast agent iopromide. The same observation was made by Cremers et al., Clin. Res. Cardiol., 2008, 97—Supp1.1.

Nowadays, it is known that active agents can be applied to a balloon catheter with various matrix-substances, including substances such as the terpenoid shellolic acid. The active agents are released during the balloon inflation at the stenosis, in order to penetrate the arterial wall segment, in order to evolve their antiproliferative and anti-inflammatory effects on the smooth muscle cells and to suppress proliferation in the vessel lumen.

The international patent application WO 2004/028582 A1 discloses multifold balloons which are coated, especially within the folds, with a composition of a pharmacological agent and a contrast medium. A method for spray coating catheter balloons is described in WO 2004/006976 A1.

It is an objective of the present invention to apply at least one active agent onto a catheter balloon in such a manner that a coating is created which can be effectively transferred to the vessel wall but is easily detached from the balloon during inflation so that a therapeutic effect concerning reduction of restenosis can be achieved best.

Said objective is solved by the technical teaching of the independent claims. Further advantageous embodiments of the invention result from the dependent claims, the description, the figures and the examples.

Surprisingly it has been found that a catheter balloon comprising a coating with an active agent and a top coat of a polyvinyl alcohol-polyethylene glycol graft copolymer is suited for resolving said objective. Preferably the top coat does not comprise any active agent.

Thus the present invention relates to catheter balloons with a coating comprising at least one active agent and a top coat consisting of a polyvinyl alcohol-polyethylene glycol graft copolymer or in other words the present invention relates to catheter balloons with a coating of at least one active agent and a top coat consisting of a polyvinyl alcohol-polyethylene glycol graft copolymer. Still in other words the present invention is directed to catheter balloons coated with at least one active agent and a top coat consisting of a polyvinyl alcohol-polyethylene glycol graft copolymer or alternatively to catheter balloons coated with at least one active agent and a top coat on said active agent coat consisting of a polyvinyl alcohol-polyethylene glycol graft copolymer.

The top coat consists preferably of a polyvinyl alcohol-polyethylene glycol graft copolymer and thus does preferably not contain any active substance or any other ingredient or component of the coating. The active agent layer or also named as active agent coat may consist of the pure active agent, preferably paclitaxel, or may comprise further components such as shellac, polyethylene glycol or a polyethoxylated surfactant or a polyethoxylated emulsifier or shellac and a polyethoxylated surfactant or shellac and a polyethoxylated emulsifier or shellac and polyethylene glycol or polyethylene glycol. The layer consisting of the active agent or comprising the active agent is below the top coat and can be directly on the balloon surface or can be applied on an additional base layer which is below the active agent layer and preferably the base layer is directly coated on the balloon surface.

Further it has been found that a catheter balloon comprising a coating with an active agent, a top coat and further comprising a polyethoxylated surfactant or a polyethoxylated emulsifier is especially suited for resolving the above-mentioned objective.

The invention is also directed to a catheter balloon with a coating comprising at least one active agent and optionally shellac or optionally a polyethoxylated surfactant and a top coat consisting of a polyvinyl alcohol-polyethylene glycol graft copolymer. It is preferred that the coating with an active agent comprises further polyethylene glycol, a polyethoxylated surfactant or a polyethoxylated emulsifier. The top coat is applied to protect the coating of the active agent from premature dissolution and mechanical damage. Therefore the top coat is advantageous, because it protects the coating from a "wash off" effect and saves it for the instant release of active agent at the position of action.

Particularly preferred are catheter balloons with a top coat of a polyvinyl alcohol-polyethylene glycol graft copolymer consisting of 75% polyvinyl alcohol units and 25% polyethylene glycol units. A polyethylene glycol chain forms a base onto which side chains of polyvinyl alcohol are grafted. Thereby the graft polymer comprises ethylene glycol monomer units and alcohol bound monomer units in a ratio of 25:75. It is further preferred that the polyvinyl alcohol-polyethylene glycol graft copolymer has an average molecular weight within the range of 40,000 Daltons to 50,000 Daltons, a melting point of 190° C.-210° C., more preferably of 195° C.-205° C. and most preferably a melting point of approximately 200° C. and is represented by the following formula which shows a characteristic part of said graft copolymer:

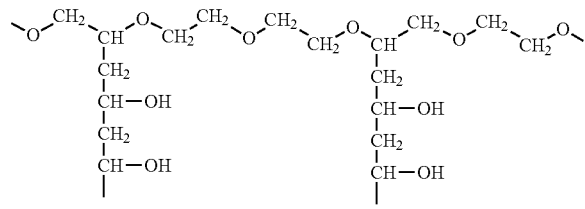

Said graft copolymer of the top coat may also comprise 0.1% to 0.5%, preferably 0.3%, colloidal silica to improve its flow properties. The preferred polyvinyl alcohol-polyethylene glycol graft copolymer dissolves readily in acidic, neutral and alkaline aqueous media, wherein the resulting solutions have a comparatively low viscosity. The molecular weight of the graft copolymer is between 30,000 Daltons to 60,000 Daltons, more preferred between 40,000 Daltons to 50,000 Daltons, still more preferred between 42,000 and 48,000 Dalton and is most preferably around 44,000-46,000 Daltons. A clear colourless flexible film remains after evaporation of the water, when an aqueous solution of the graft copolymer is applied on a smooth surface. Other preferred variations of top coat components can comprise polyvinyl acetate dispersion (27%) stabilized with povidone (2.7%) and sodium lauryl sulphate (0.3%) or methyl methacrylate and diethylaminoethyl methacrylate copolymer dispersion, wherein the solids concentration is approximately 30%.

A particularly preferred embodiment of the present invention is a catheter balloon with a coating comprising paclitaxel and a top coat consisting of a polyvinyl alcohol-polyethylene glycol graft copolymer. In one embodiment of the invention the material of the top coat is also present in the active-agent layer where it is mixed with the active agent.

It is also possible to apply one or more additional additives as a carrier, excipient or second matrix substance to the surface of the catheter, balloon according to the invention. There are, for example, biologically compatible organic substances that improve the coating properties and increase the uptake of the active agent and especially of paclitaxel into the vessel, such as sugar and proteins like albumin or resins especially dammar, mastic, rosin or shellac. It is particularly preferred that the at least one additive is shellac. Nevertheless it is preferred that the coating of the catheter balloon according to the invention does not comprise contrast agents, at least the active agent containing layer preferably does not contain contrast agents. Moreover the coating of the catheter balloon of the present invention does not contain plasticizers such as acetyl tributyl citrate or acetyl triethyl citrate and does also not contain any citrate esters. Also excluded from the present invention are the components sorbitol, sorbic acid, sorbates, sorbic acid esters, and any polysorbates. These substances are not used within the present invention.

Therefore the present invention relates to a catheter balloon coated with a coating of at least one active agent and a top coat consisting of a polyvinyl alcohol-polyethylene glycol graft copolymer wherein the coating further comprises shellac.

Particularly preferred as a matrix for the active agent and especially paclitaxel is a combination of at least one polyethoxylated surfactant or a polyethoxylated emulsifier together with shellac so that the present invention relates to a catheter balloon coated with a coating of at least one active agent in a layer of at least one polyethoxylated surfactant or a polyethoxylated emulsifier with shellac and a top coat consisting of a polyvinyl alcohol-polyethylene glycol graft copolymer. Further preferred as a matrix for the active agent and especially paclitaxel is a combination of polyethylene glycol together with shellac so that the present invention relates to a catheter balloon coated with a coating of at least one active agent in a layer of polyethylene glycol with shellac and a top coat consisting of a polyvinyl alcohol-polyethylene glycol graft copolymer. Also preferred as a matrix for the active agent and especially paclitaxel is a combination of at least one polyethoxylated surfactant or a polyethoxylated emulsifier together with polyethylene glycol so that the present invention relates to a catheter balloon coated with a coating of at least one active agent in a layer of at least one polyethoxylated surfactant or a polyethoxylated emulsifier with polyethylene glycol and a top coat consisting of a polyvinyl alcohol-polyethylene glycol graft copolymer. This produces a coating which easily and quickly detaches from the catheter balloon and can effectively be transferred to the vessel wall.

The catheter balloon of the invention may optionally comprise further a base coat. It was surprisingly found that such a base coat is therapeutically highly useful in keeping blood vessels open, in reducing the late lumen loss and in reducing restenosis. The base coat is apparently useful by facilitating a better transfer of the active agent from the catheter balloon to the vessel wall. The base coat may used for a coating with an active agent layer consisting only of the active agent or comprising the active agent and at least one polyethoxylated surfactant or a polyethoxylated emulsifier. Eventually also shellac or polyethylene glycol may be one component of this active agent containing layer.

Preferred embodiments of the invention comprise a base coat made of polyvinyl alcohol-polyethylene glycol graft copolymer or shellac. Therefore one embodiment of the present invention relates to a catheter balloon coated with at least one active agent and a top coat consisting of a polyvinyl alcohol-polyethylene glycol graft copolymer wherein the coating further comprises a base coat on said catheter balloon consisting of polyvinyl alcohol-polyethylene glycol graft copolymer and/or shellac. Another preferred embodiment is a catheter balloon coated with at least one active agent a matrix for the drug-coating of a catheter balloon of at least one polyethoxylated surfactant or a polyethoxylated emulsifier and a top coat consisting of a polyvinyl alcohol-polyethylene glycol graft copolymer wherein the coating further comprises a base coat of shellac or of polyvinyl alcohol-polyethylene glycol graft copolymer or a mixture of these two compounds. Another preferred embodiment is a catheter balloon coated with at least one active agent a matrix for the drug-coating of a catheter balloon of polyethylene glycol optionally with shellac and a top coat consisting of a polyvinyl alcohol-polyethylene glycol graft copolymer wherein the coating further comprises a base coat of shellac or of polyvinyl alcohol-polyethylene glycol graft copolymer or a mixture of these two compounds. In a particular preferred embodiment of the present invention, the catheter balloon which is completely coated with the top coat, but is coated with active agent only partially, i.e. certain sections of the catheter balloon, has a base coat on the complete outer surface.

A particular preferred embodiment of the present invention is a catheter balloon with a coating comprising paclitaxel and a top coat consisting of a polyvinyl alcohol-polyethylene glycol graft copolymer and a base coat on said catheter balloon consisting of polyvinyl alcohol-polyethylene glycol graft copolymer and/or shellac. Further preferred is a catheter balloon coated with paclitaxel a matrix for the active agent coating of a catheter balloon of at least one polyethoxylated surfactant or a polyethoxylated emulsifier and a top coat consisting of a polyvinyl alcohol-polyethylene glycol graft copolymer, wherein the coating further comprises a base coat of shellac or of polyvinyl alcohol-polyethylene glycol graft copolymer or a mixture of these two compounds. Another preferred embodiment is a catheter balloon coated with paclitaxel a matrix for the active agent coating of a catheter balloon of polyethoxylated castor oil and a top coat consisting of a polyvinyl alcohol-polyethylene glycol graft copolymer wherein the coating further comprises a base coat of shellac or of polyvinyl alcohol-polyethylene glycol graft copolymer or a mixture of these two compounds. One further embodiment is a catheter balloon coated with paclitaxel a matrix for the drug-coating of a catheter balloon of polyethylene glycol optionally with shellac and a top coat consisting of a polyvinyl alcohol-polyethylene glycol graft copolymer wherein the coating further comprises a base coat of shellac or of polyvinyl alcohol-polyethylene glycol graft copolymer or a mixture of these two compounds.

Thus, all embodiments of the present invention comprise a top coat which is on top of the layer consisting of or comprising the active agent which is preferably paclitaxel. This top coat preferably covers completely the below layer of the active agent or containing the active agent. The top coat consists of a polyvinyl alcohol-polyethylene glycol graft copolymer and does preferably not contain any active agent and also not any polyethoxylated surfactant or polyethoxylated emulsifier and also no shellac. This special kind of top coat seems to be important to secure the coating on the catheter balloon and to prevent wash off and release of the active agent, especially paclitaxel, during insertion of the to the stenotic vessel region, but also to ensure and support the transfer of the active agent to and into the vessel during dilatation. Consequently, the polyvinyl alcohol-polyethylene glycol graft copolymer top coat seems to be an essential part of the present invention.

Moreover below the top coat a coat or layer of pure active agent can be present or a coat or layer comprising the active agent together with shellac or with a polyethoxylated surfactant which is preferably polyethoxylated castor oil or with polyethylene glycol or together with shellac and a polyethoxylated surfactant or with polyethylene glycol and shellac or with polyethylene glycol and a polyethoxylated surfactant.

Furthermore below this coat or layer consisting of the active agent or consisting of the active agent together with shellac, together with polyethylene glycol or together with the polyethoxylated surfactant or together with shellac and the polyethoxylated surfactant, a third coat or layer can be optionally present. This third coat or layer also named base layer consists of a polyethoxylated surfactant or of shellac or of a polyethoxylated surfactant and shellac. In case a polyethoxylated surfactant is used in or as the base coat and also together with the active agent in the active agent layer, preferably the same polyethoxylated surfactant is used which is preferably polyethoxylated castor oil.

Consequently the following coatings are in accordance with the present invention:

I) Balloon surface coated with paclitaxel and with polyvinyl alcohol-polyethylene glycol graft copolymers as top coat.

II) Balloon surface coated with paclitaxel together with shellac and with polyvinyl alcohol-polyethylene glycol graft copolymers as top coat.

III) Balloon surface coated with paclitaxel together with polyethoxylated castor oil and with polyvinyl alcohol-polyethylene glycol graft copolymers as top coat.

IV) Balloon surface coated with paclitaxel together with polyethylene glycol and with polyvinyl alcohol-polyethylene glycol graft copolymers as top coat.

V) Balloon surface coated with paclitaxel together with shellac as well as polyethoxylated castor oil and with polyvinyl alcohol-polyethylene glycol graft copolymers as top coat.

VI) Balloon surface coated with paclitaxel together with shellac as well as polyethylene glycol and with polyvinyl alcohol-polyethylene glycol graft copolymers as top coat.

VII) Balloon surface coated with shellac as base coat, then with paclitaxel as middle coat and with polyvinyl alcohol-polyethylene glycol graft copolymers as top coat.
VIII) Balloon surface coated with shellac as base coat, then with paclitaxel together with shellac as middle coat and with polyvinyl alcohol-polyethylene glycol graft copolymers as top coat.
IX) Balloon surface coated with shellac as base coat, then with paclitaxel together with polyethoxylated castor oil as middle coat and with polyvinyl alcohol-polyethylene glycol graft copolymers as top coat.
X) Balloon surface coated with shellac as base coat, then with paclitaxel together with polyethylene glycol as middle coat and with polyvinyl alcohol-polyethylene glycol graft copolymers as top coat.
XI) Balloon surface coated with shellac as base coat, then with paclitaxel together with shellac as well as polyethoxylated castor oil as middle coat and with polyvinyl alcohol-polyethylene glycol graft copolymers as top coat.
XII) Balloon surface coated with shellac as base coat, then with paclitaxel together with shellac as well as polyethylene glycol as middle coat and with polyvinyl alcohol-polyethylene glycol graft copolymers as top coat.
XIII) Balloon surface coated with polyethoxylated castor oil as base coat, then with paclitaxel as middle coat and with polyvinyl alcohol-polyethylene glycol graft copolymers as top coat.
XIV) Balloon surface coated with polyethoxylated castor oil as base coat, then with paclitaxel together with shellac as middle coat and with polyvinyl alcohol-polyethylene glycol graft copolymers as top coat.
XV) Balloon surface coated with polyethoxylated castor oil as base coat, then with paclitaxel together with polyethoxylated castor oil as middle coat and with polyvinyl alcohol-polyethylene glycol graft copolymers as top coat.
XVI) Balloon surface coated with polyethoxylated castor oil as base coat, then with paclitaxel together with shellac as well as polyethoxylated castor oil as middle coat and with polyvinyl alcohol-polyethylene glycol graft copolymers as top coat.
XVII) Balloon surface coated with shellac and polyethoxylated castor oil as base coat, then with paclitaxel as middle coat and with polyvinyl alcohol-polyethylene glycol graft copolymers as top coat.
XVIII) Balloon surface coated with shellac and polyethoxylated castor oil as base coat, then with paclitaxel together with shellac as middle coat and with polyvinyl alcohol-polyethylene glycol graft copolymers as top coat.
XIX) Balloon surface coated with shellac and polyethoxylated castor oil as base coat, then with paclitaxel together with polyethoxylated castor oil as middle coat and with polyvinyl alcohol-polyethylene glycol graft copolymers as top coat.
XX) Balloon surface coated with shellac and polyethoxylated castor oil as base coat, then with paclitaxel together with shellac as well as polyethoxylated castor oil as middle coat and with polyvinyl alcohol-polyethylene glycol graft copolymers as top coat.
XXI) Balloon surface coated with shellac and polyethoxylated castor oil as base coat, then with paclitaxel together with shellac as well as polyethylene glycol oil as middle coat and with polyvinyl alcohol-polyethylene glycol graft copolymers as top coat.

Or in other words:
I) First layer paclitaxel and top coat polyvinyl alcohol-polyethylene glycol graft copolymer.
II) First layer paclitaxel together with shellac and top coat polyvinyl alcohol-polyethylene glycol graft copolymer.
III) First layer paclitaxel together with polyethoxylated castor oil and top coat polyvinyl alcohol-polyethylene glycol graft copolymer.
IV) First layer paclitaxel together with polyethylene glycol and top coat polyvinyl alcohol-polyethylene glycol graft copolymer.
V) First layer paclitaxel together with shellac as well as polyethoxylated castor oil and top coat polyvinyl alcohol-polyethylene glycol graft copolymer.
VI) First layer paclitaxel together with shellac as well as polyethylene glycol and top coat polyvinyl alcohol-polyethylene glycol graft copolymer.
VII) Base coat shellac, middle coat paclitaxel, top coat polyvinyl alcohol-polyethylene glycol graft copolymer.
VIII) Base coat shellac, middle coat paclitaxel together with shellac, top coat polyvinyl alcohol-polyethylene glycol graft copolymer.
IX) Base coat shellac, middle coat paclitaxel together with polyethoxylated castor oil, top coat polyvinyl alcohol-polyethylene glycol graft copolymer.
X) Base coat shellac, middle coat paclitaxel together with polyethylene glycol, top coat polyvinyl alcohol-polyethylene glycol graft copolymer.
XI) Base coat shellac, middle coat paclitaxel together with shellac as well as polyethoxylated castor oil, top coat polyvinyl alcohol-polyethylene glycol graft copolymer.
XII) Base coat polyethoxylated castor oil, middle coat paclitaxel, top coat polyvinyl alcohol-polyethylene glycol graft copolymer.
XIII) Base coat polyethoxylated castor oil, middle coat paclitaxel together with shellac, top coat polyvinyl alcohol-polyethylene glycol graft copolymer.
XIV) Base coat polyethoxylated castor oil, middle coat paclitaxel together with polyethylene glycol, top coat polyvinyl alcohol-polyethylene glycol graft copolymer.
XV) Base coat polyethoxylated castor oil, middle coat paclitaxel together with polyethoxylated castor oil, top coat polyvinyl alcohol-polyethylene glycol graft copolymer.
XVI) Base coat polyethoxylated castor oil, middle coat paclitaxel together with shellac as well as polyethoxylated castor oil, top coat polyvinyl alcohol-polyethylene glycol graft copolymer.
XVII) Base coat shellac and polyethoxylated castor oil, middle coat paclitaxel, top coat polyvinyl alcohol-polyethylene glycol graft copolymer.
XVIII) Base coat shellac and polyethoxylated castor oil, middle coat paclitaxel together with shellac, top coat polyvinyl alcohol-polyethylene glycol graft copolymer.
XIX) Base coat shellac and polyethoxylated castor oil, middle coat paclitaxel together with polyethylene glycol, top coat polyvinyl alcohol-polyethylene glycol graft copolymer.
XX) Base coat shellac and polyethoxylated castor oil, middle coat paclitaxel together with polyethoxylated castor oil, top coat polyvinyl alcohol-polyethylene glycol graft copolymer.
XXI) Base coat shellac and polyethoxylated castor oil, middle coat paclitaxel together with shellac as well as polyethoxylated castor oil, top coat polyvinyl alcohol-polyethylene glycol graft copolymer.

XXII) Base coat shellac and polyethoxylated castor oil, middle coat paclitaxel together with shellac as well as polyethylene glycol, top coat polyvinyl alcohol-polyethylene glycol graft copolymer.

Shellac is a natural resin produced from the glandular secretion of a number of species of lac-producing insects. Lac insects belong to the order of Hemiptera, superfamily Coccoidea such as Metatachardia, *Laccifer*, Tachordiella, and others, however, members of two families—Lacciferidae and Tachardinidae are more prominent in lac secretion. The one that is commercially cultured is *Kerria lacca*, which is also known by such synonyms as *Laccifer lacca* Ker, *Tachardia lacca*, and *Carteria lacca*. *Kerria lacca* is an Indian scale insect, which infests branches of numerous trees from the East Indies, such as *Butea frondos* Rosch, *Acacia arabica* Willd and *Ficus religiosa* Linn. Shellac is the only commercially used natural resin of animal origin and is quite different from all other natural resins. More recently, as a new awareness about the environments and the toxicity of chemical raw-material is noticeable everywhere, shellac or shellac modified resin are gaining importance due to their interesting and unique characteristics. Broken branches are sold as stick lac and, after grounding and washing with water to eliminate wood and red pigments (lac dye), seed lac is obtained. Purification of seed lac gives the more homogeneous product known as shellac. Its use in Europe began towards the end of the 16$^{th}$ century mainly as a varnish (mostly known as "French polish") for wooden objects, musical instruments and gilding, as a protective for vinyl disks and mural paintings, as an insulating material for earlier radios and other electrical tools and as an adhesive in the restoration of pottery.

Raw material shellac consists of 70-80% resin, 4-8% dye, 6-7% hard and high gloss finished wax, 3% water, up to 9% vegetable and animal impurities and aroma substances. Shellac resin is a complicated mixture of aliphatic (60%) and sesquiterpenoid acids (32%) and their esters. Sesquiterpenoid acids are jalaric and laccijalaric acids (structure I and II) and aliphatic acids are aleuritic (III) and butolic acid.

A possibility for chemical description of resin molecule is a structure model where in each case 4 molecules jalaric or laccijalaric acid and aleuritic acid are connected by ester bonding alternately.

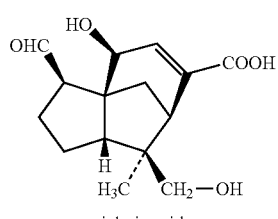

jalaric acid (I)

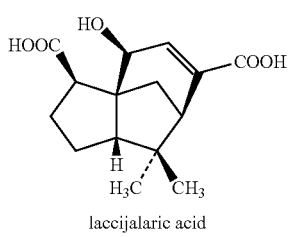

laccijalaric acid (II)

Its chemical composition is almost constant, although the amount of some components changes depending on the nature of host trees on which the insects grows. By Cannizzaro-type disproportionation under alkaline hydrolysis will be synthesized from these acids shellolic acid (IV) and deviate compounds. Purified shellac consists of two main components. These components are 9,10,16-trihydroxypalmitic acid (aleuritic acid) CAS [53-387-9] and shellolic acid (IV).

$$HO-CH_2-(CH_2)_5-CH-CH-(CH_2)_7-COOH$$
$$\underset{OH}{|} \quad \underset{OH}{|}$$

aleuritic acid (III)

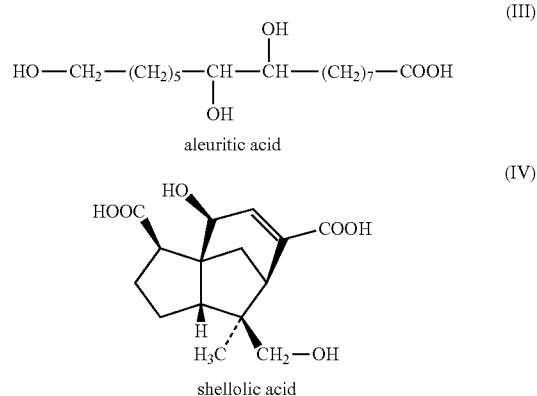

shellolic acid (IV)

A modification with other natural or synthetic resins or co-polymerization with various monomers is possible to cross link shellac, modified shellac resins and shellac copolymers with urea, melamine, formaldehyde, isocyanides, other chemical processes like polymerization, hydroxylation, extrication, etc. are possible.

Followings are the commercial grades of shellac:

| | |
|---|---|
| Seedlac | Dewaxed Shellac |
| Hand Made Shellac | Dewaxed Bleached Shellac |
| Machine Made Shellac | Aleuritic Acid |

Major Properties of shellac are:
Shellac is a hard natural resin
Shellac has a good resistance against solvent
Shellac based on hydrocarbons
Shellac is non toxic
Shellac is thermoplastic
Shellac is physiologically harmless
Shellac is approved for various applications in the food industry.
Shellac is not UV-resistant
Shellac is soluble in lower alcohol's
Shellac has excellent dielectric properties high dielectric strength, low dielectric constant, good tracking resistance etc.
Shellac has a low melting point (65-85° C.).
Shellac is water soluble in water-alkaline solutions
Coatings do not change their electric properties under UV-radiation.
Shellac has excellent film forming properties.
Shellac has low thermal conductivity and a low coefficient of expansion forms smooth, high gloss films and surfaces.
Shellac coating has excellent adhesion to many coatings and can be polished.

A possibility for chemical description of resin molecule is a structure model where in each case 4 molecules jalaric or laccijalaric acid and aleuritic acid are connected by ester bonding alternately.

The term "base coat" as used herein refers to a layer of the coating of a catheter balloon which is immediately on the surface of the catheter balloon. This layer is a first layer which directly overlays the material of the catheter balloon as a priming coat which mainly increases the adherence of the active agent containing layer. The term "top layer" or "top coat" as used herein refers to a layer of the balloon coating free of an active agent which overlays the active agent containing layer.

The term "uncoated" as used herein refers to a catheter balloon with a smooth or structured or roughened surface without any active agent coating, i.e. the balloon surface does not comprise a pharmaceutically active agent and especially no antiproliferative, immunosuppressive, anti-angiogenic, anti-inflammatory, anti-restenotic, or anti-thrombotic agent and no coating containing an antiproliferative, immunosuppressive, anti-angiogenic, anti-inflammatory, anti-restenotic, and/or anti-thrombotic agent.

The present invention refers to a catheter balloon coated with at least one active agent and a top coat on said active agent coat consisting of a polyvinyl alcohol-polyethylene glycol graft copolymer. Materials used for the balloon of the catheter are such materials which are commonly used, wherein the following polymers are particularly preferred: polyamides, block copolymers of polyamide, polyether and polyester, polyurethanes, polyesters and polyolefins.

The catheter balloon of the invention is dilatable or expandable and is most preferably an angioplasty catheter balloon. The present invention relates to dilatable and expandable catheter balloons and in particular to multifold balloons for catheters. Such catheters or catheter balloons having a coating according to the invention are preferably used for treating constricted vessel segments, particularly of blood vessels, coronary vessels as well as peripheral vessels, and for the treatment and prophylaxis of stenosis, restenosis, arteriosclerosis and fibrotic vessel constriction.

Any commercially available dilatable catheter balloon may be used as catheter balloon. Such balloons are commonly provided with folds or wings forming essentially closed cavities when the balloon is in its compressed state but bending outward during dilatation and being capable of releasing substances contained in the folds or respectively of pressing said substances against the vessel wall.

Such balloons are advantageous since the substances enclosed in the folds or respectively paclitaxel enclosed in the folds are protected from being detached too soon during the insertion of the catheter. The surface of the catheter balloon may be textured, smooth, rough, harsh, provided with cavities or provided with channels open towards the outside of the balloon. In the case, a textured surface of the catheter balloon is desired the surface of the catheter balloon can be textured mechanically, chemically, electronically and/or by means of radiation to allow for an improved adhesion of paclitaxel and to assist the precipitation or crystallization of the paclitaxel. It is of importance to avoid all damage to the catheter balloons while the balloon surface is textured and to ensure that their capability to expand is not disadvantageously affected. Thus, the methods for micro texturing the balloon surface must not lead to the formation of holes, micropores or fissures in the balloon material. Ideally, only the outer surface of the balloon, i.e. to a maximum depth of 1 µm, is textured.

The inventive catheter balloon can be used without or with a crimped stent while without stent is preferred. As stent, all kinds of common stents, such as self-expandable stents, not self-expandable stents, metal stents, polymer stents, biodegradable stents, bifurcation stents, uncoated (bare) stents, polymer coated stents, drug release coated stents, stents with a pure active agent coating etc. can be used.

Moreover, the stent can be crimped on the catheter balloon before the inventive coating procedure is carried out so that catheter balloon and stent are coated together with an active agent coating according to the invention. However, it is preferred to use the coated catheter balloon of the present invention without stent.

One embodiment of the invention is a catheter balloon coated with at least one active agent and a top coat consisting of a polyvinyl alcohol-polyethylene glycol graft copolymer. Preferred embodiments of the invention have a coating comprising at least one polyethoxylated surfactant or at least one polyethoxylated emulsifier. The at least one polyethoxylated surfactant or at least one polyethoxylated emulsifier may be applied to the catheter balloon either before the active agent is applied or the at least one polyethoxylated surfactant or at least one polyethoxylated emulsifier is applied together with the active agent, which means that one coating solution comprises the active agent and the at least one polyethoxylated surfactant or at least one polyethoxylated emulsifier. Therefore one embodiment of the invention is a catheter balloon coated with at least one active agent in a matrix comprising at least one polyethoxylated surfactant or at least one polyethoxylated emulsifier. The term matrix is used in this application for a compound the active agent is embedded in or incorporated in.

The term "emulsifier" as used herein is a substance that stabilizes an emulsion by increasing its kinetic stability. An emulsion is a mixture of two or more liquids which are normally immiscible. With other words, emulsifiers are excipients or additives, which serve for mixing two liquids which may not be mixed with each other in a so-called emulsion and to stabilize the latter. Similar to emulsifiers are so called "surfactants". The term as used herein refers to compounds that lower the surface tension of a liquid, the interfacial tension between two liquids, or that between a liquid and a solid. Surfactants may act as detergents, wetting agents, emulsifiers, foaming agents, and dispersants. Emulsifiers and surfactants, respectively, are usually organic compounds that are amphiphilic, meaning they contain both hydrophobic groups and hydrophilic groups. Consequently an amphiphilic molecule contains both a water insoluble component and a water soluble component. Emulsifiers and surfactants as used herein are classified according to the composition of their hydrophilic part. Emulsifiers and surfactants, respectively, suitable for the present invention are aromatic hydrocarbons, alkanes, alkenes, cycloalkanes, alkyne-based hydrocarbons, fluorosurfactants such as perfluorooctanesulfonic acid, perfluorooctanoic acid, perfluorononanoic acid and siloxane being polyethoxylated. Ethoxylation is a chemical process in which ethylene oxide is added to alcohols and phenols to generate surfactants and emulsifiers. Consequently polyethoxylation is a chemical process wherein more than one group of the respective alcohol or phenol are ethoxylated. Polyethoxylated compounds are preferred emulsifiers and surfactants, respectively, in the present invention; more preferred are polyethoxylated surfactants or polyethoxylated emulsifiers selected from the group consisting of or comprising: polyethoxylated alcohols, polyethoxylated oils, polyethoxylated castor oil, polyethoxylated glycerol, polyethoxylated fatty acid esters, polyethoxylated phenols, polyethoxylated amines and polyethoxylated fatty alcohols. Among these surfactants or emulsifiers polyethoxylated castor oils are more preferred. Further preferred are compounds which are produced by reacting higher saturated fatty alcohols with ethylene oxide, and particularly preferred are compounds which are made by reacting castor oil with ethylene oxide in a ration of 1:35, which means that it is prepared by reacting 35 moles of ethylene oxide with each mol of castor oil. Thereby the hydroxyl-groups of the castor oil triglyceride have ethoxylated with ethylene oxide to from polyethylene glycol ethers. This is followed by a purification process with regard to water content, potassium ions and free fatty acids, particularly ricinoleic, oleic and palmitic acids. The compound received is a white to yellowish paste or cloudy liquid. On heating, the last solid constituents melt at 26° C. to yield a clear oily liquid with a weak but characteristic odour. The HLB (hydrophilic-lipophilic balance) value lies between 12 and 14. The critical micelle concentration (CMC) lies at approx. 0.02%. Said preferred polyethoxylated castor oil is also named macrogolglycerol ricinoleate Ph. Eur., Polyoxyl-35-castor oil USP/NF and is distributed under the trademark Cremophor® ELP by BASF.

Further components for improving the emulsifying properties of the latter two components can be polyethylene glycol esters of ricinoleic acid, polyethylene glycols and polyethylene glycol esters of glycerol.

Polyethoxylated fatty alcohols and polyethoxylated castor oil are dissolved in water and alcohol to form either a colloid or a clear solution. The compounds are soluble in vegetable and mineral oils and fats. The warm emulsifiers can be mixed with mineral, vegetable and synthetic fats and oils, as well as with fatty alcohols, fatty acids, mono- and di-stearates, and polyethylene glycols. In aqueous solution, these compounds are largely resistant to acids, bases and salts. The presence of these electrolytes does not impair the product's efficiency as emulsifying agent. The particularly preferred polyethoxylated castor oil dissolves in a wide range of further organic solvents, such as ethanol, n-propanol, isopropanol, ethyl acetate, chloroform, carbon tetrachloride, trichloroethylene, toluene and xylene.

One embodiment of the invention is a catheter balloon coated with at least one active agent and a top coat consisting of a polyvinyl alcohol-polyethylene glycol graft copolymer. Preferred embodiments of the invention have a coating comprising further polyethylene glycol. According to the invention polyethylene glycol may be applied to the balloon surface as a matrix substance for the at least one active agent.

Polyethylene glycol may be used alone or together with shellac or together with the t least one polyethoxylated surfactant.

Antiproliferative, immunosuppressive, anti-angiogenic, anti-inflammatory, anti-restenotic and/or anti-thrombotic agent are used as active agents. The active agents are used individually or combined having same or different concentration. These active agents can be applied to the surface of the catheter balloon forming a pure active agent layer without any matrix but being at least covered by the top coat of the invention. It is also possible, that the active agent is applied being dissolved, emulsified, suspended or dispersed in the at least one polyethoxylated surfactant or polyethoxylated emulsifier and/or shellac and/or polyethylene glycol. Such an inclusion of the active agents ensures that a short-term and controlled release of the active agents from the matrix takes place by the balloon dilatation during in vasodilation. Further, there is the possibility, that the active agent or the combination of active agents is applied to the surface after coating of the catheter balloon with the at least one polyethoxylated surfactant or polyethoxylated emulsifier and/or shellac and/or polyethylene glycol and is the soaked into this layer on the surface of the catheter balloon.

Preferred is a coated catheter balloon, wherein the active agent is an antiproliferative, immunosuppressive, anti-angiogenic, anti-inflammatory, anti-restenotic and/or anti-thrombotic agent. It is further preferred if the active agent is selected from the group consisting of or comprising: abciximab, acemetacin, acetylvismione B, aclarubicin, ademetionine, adriamycin, aescin, afromosone, akagerine, aldesleukin, amidorone, aminoglutethimide, amsacrine, anakinra, anastrozole, anemonin, anopterine, antimycotics antithrombotics, apocymarin, argatroban, aristolactam-All, aristolochic acid, ascomycin, asparaginase, aspirin, atorvastatin, auranofin, azathioprine, azithromycin, baccatin, bafilomycin, basiliximab, bendamustine, benzocaine, berberine, betulin, betulinic acid, bilobol, bisparthenolidine, bleomycin, combrestatin, Boswellic acids and derivatives thereof, bruceanol A, B and C, bryophyllin A, busulfan, antithrombin, bivalirudin, cadherins, camptothecin, capecitabine, o-carbamoyl-phenoxyacetic acid, carboplatin, carmustine, celecoxib, cepharanthin, cerivastatin, CETP inhibitors, chlorambucil, chloroquine phosphate, cicutoxin, ciprofloxacin, cisplatin, cladribine, clarithromycin, colchicine, concanamycin, coumadin, C-type natriuretic peptide (CNP), cudraisoflavone A, curcumin, cyclophosphamide, ciclosporin A, cytarabine, dacarbazine, daclizumab, dactinomycin, dapsone, daunorubicin, diclofenac, 1,11-dimethoxycanthin-6-one, docetaxel, doxorubicin, daunamycin, epirubicin, erythromycin, estramustine, etoposide, filgrastim, fluroblastin, fluvastatin, fludarabine, fludarabine-5'-dihydrogen phosphate, fluorouracil, folimycin, fosfestrol, gemcitabine, ghalakinoside, ginkgol, ginkgolic acid, glycoside 1a, 4-hydroxyoxycyclo phosphamide, idarubicin, ifosfamide, josamycin, lapachol, lomustine, lovastatin, melphalan, midecamycin, mitoxantrone, nimustine, pitavastatin, pravastatin, procarbazine, mitomycin, methotrexate, mercaptopurine, thioguanine, oxaliplatin, irinotecan, topotecan, hydroxycarbamide, miltefosine, pentostatin, pegaspargase, exemestane, letrozole, formestane, mycophenolate mofetil, β-lapachone, podophyllotoxin, podophyllic acid-2-ethyl hydrazide, molgramostim (rhuGM-CSF), peginterferon α-2b, lenograstim (r-HuG-CSF), macrogol, selectin (cytokine antagonist), cytokinin inhibitors, COX-2 inhibitor, angiopeptin, monoclonal antibodies inhibiting muscle cell proliferation, bFGF antagonists, probucol, prostaglandins, 1-hydroxy-11-methoxycanthin-6-one, scopoletin, NO donors, pentaerythrityl tetranitrate and sydnoimines, S-nitroso derivatives, tamoxifen, staurosporine, β-estradiol, α-estradiol, estriol, estrone, ethinyl estradiol, medroxyprogesterone, estradiol cypionates, estradiol benzoates, tranilast, kamebakaurin and other terpenoids used in cancer therapy, verapamil, tyrosine kinase inhibitors (tyrphostins), paclitaxel and derivatives thereof, 6-α-hydroxy-paclitaxel, taxoteres, mofebutazone, lonazolac, lidocaine, ketoprofen, mefenamic acid, piroxicam, meloxicam, penicillamine, hydroxychloroquine, sodium aurothiomalate, oxaceprol, β-sitosterol, myrtecaine, polidocanol, nonivamide, levomenthol, ellipticine, D-24851 (Calbiochem), colcemid, cytochalasin A-E, indanocine, nocodazole, bacitracin, vitronectin receptor antagonists, azelastine, guanidyl cyclase stimulator, tissue inhibitor of metal proteinase-1 and -2, free nucleic acids, nucleic acids incorporated into virus transmitters, DNA and RNA fragments, plasminogen activator inhibitor 1, plasminogen activator inhibitor 2, antisense oligonucleotides, VEGF inhibitors, IGF-1, active agents from the group of antibiotics, cefadroxil, cefazolin, cefaclor, cefoxitin, tobramycin, gentamicin, penicillins, dicloxacillin, oxacillin, sulfonamides, metronidazole, enoxaparin, heparin, hirudin, PPACK, protamine, prourokinase, streptokinase, warfarin, urokinase, vasodilators, dipyramidole, trapidil, nitroprussides, PDGF antagonists, triazolopyrimidine, seramin, ACE inhibitors, captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators, halofuginone, nifedipine, tocopherol, tranilast, molsidomine, tea polyphenols, epicatechin gallate, epigallocatechin gallate, leflunomide, etanercept, sulfasalazine, tetracycline, triamcinolone, mutamycin, procainimide, retinoic acid, quinidine, disopyrimide, flecainide, propafenone, sotalol, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS), fenoprofen, ibuprofen, indomethacin, naproxen, phenylbutazone, antiviral agents, acyclovir, ganciclovir zidovudine, clotrimazole, flucytosine, griseofulvin, ketoconazole, miconazole, nystatin, terbinafine, antiprotozoal agents, chloroquine, mefloquine, quinine, natural terpenoids, hippocaesculin, barringtogenol-C21-angelate, 14-dehydroagrostistachin, agroskerin, agrostistachin, 17-hydroxyagrostistachin, ovatodiolids, 4,7-oxycycloanisomelic acid baccharinoids B1, B2, B3 and B7, tubeimoside, bruceantinoside C, yadanziosides N and P, isodeoxyelephantopin, tomenphantopin A and B, coronarin A, B C and D, ursolic acid, hyptatic acid A, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, cymarin, hydroxyanopterine, protoanemonin, cheliburin chloride, sinococuline A and B, dihydronitidine, nitidine chloride, 12-β-hydroxypregnadien-3, 20-dione, helenalin, indicine, indicine-N-oxide, lasiocarpine, inotodiol, podophyllotoxin, justicidin A and B, larreatin, malloterin, mallotochromanol, isobutyrylmallotochromanol, marchantin A, maytansin, lycoridicin, margetine, pancratistatin, liriodenine, oxoushinsunine, periplocoside A, deoxypsorospermin, psychorubin, ricin A, sanguinarine, manwu wheat acid, methylsorbifolin, chromones of spathelia, stizophyllin, dihydrousambaraensine, hydroxyusambarine, strychnopentamine, strychnophylline, usambarine, usambarensine, liriodenine, daphnoretin, lariciresinol, methoxylariciresinol, syringaresinol, sirolimus (rapamycin), rapamycin derivatives, biolimus A9, pimecrolimus, everolimus, myolimus, novolimus, ridaforolimus, temsirolimus, zotarolimus, tacrolimus, fasudil, epothilones, somatostatin, roxithromycin, troleandomycin, simvastatin, rosuvastatin, vinblastine, vincristine, vindesine, teniposide, vinorelbine, trofosfamide, treosulfan, temozolomide, thiotepa, tretinoin, spiramycin, umbelliferone, desacetylvismione A, vismione A and B, zeorin.

In a preferred embodiment of the invention, a second active agent may be added to the active agent containing layer, wherein the second active agent is selected from the same group of compounds listed in the previous paragraph.

The preferred solvents for the active agents are volatile easily removable solvents such as acetone, ethyl acetate, ethanol, methanol, DMSO (dimethyl sulfoxide), THF (tetrahydrofurane), chloroform, methylene chloride.

More preferred is that the active agent of the present invention is selected from the group comprising or consisting of: paclitaxel and paclitaxel derivatives, taxanes, docetaxel, rapamycin and rapamycin derivatives, sirolimus (rapamycin), rapamycin derivatives, biolimus A9, pimecrolimus, everolimus, myolimus, novolimus, ridaforolimus, temsirolimus, zotarolimus, tacrolimus, fasudil and epothilones.

The particularly preferred active agent in the present invention is paclitaxel.

Paclitaxel is commercially available from several suppliers. Paclitaxel is known under the trademark name of TAXOL® (paclitaxel) and is also designated with various synonymous names such as: BMS 181339-01, BMS-181339, BMS-181339-01, Capxol, DRG-0190, DTS-301, Ebetaxel, Genaxol, Genexol, Genexol-PM, HSDB 6839, Intaxel, KBio2_002509, KBio2_005077, KBio2_007645, KBio3_002987, KBioGR_002509, KBioSS_002517, LipoPac, MBT 0206, MPI-5018, Nanotaxel, NCI60_000601, Nova-12005, NSC 125973, NSC-125973, NSC125973, Onxol, Pacligel, Paxceed, Paxene, Paxoral, Plaxicel, QW 8184, SDP-013, TA1, Tax-11-en-9-on, Tax-Albin, Taxol A, Xorane or Yewtaxan.

Its chemical structure is as follows:

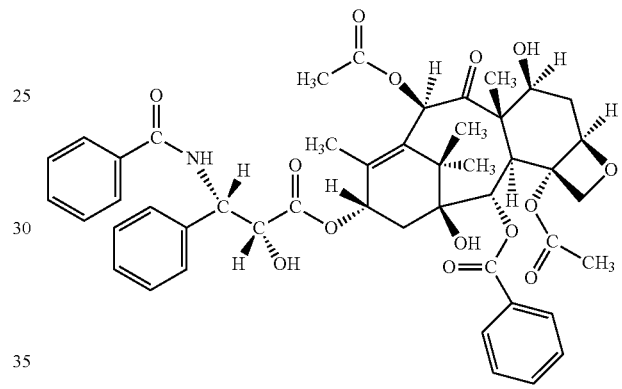

IUPAC nomenclature is: [2aR-[2a,4,4a,6,9(R*,S*),11,12,12a,12b]]-(benzoylamino)-hydroxybenzene propionic acid 6,12b-bis-(acetyloxy)-12-(benzoyloxy)-2a-3, 4, 4a,5, 6, 9, 10, 11, 12, 12a,12b-dodecahydro-4, 11-dihydroxy-4a,8, 13,13-tetramethyl-5-oxo-7,11-methano-1H-cyclodeca[3,4]benz[1,2-b]oxet-9-yl ester).

Paclitaxel is highly soluble in dimethyl sulfoxide (DMSO) and methanol as well as in anhydrous ethanol, but is comparatively poorly soluble in water. Paclitaxel is especially stable at a pH between 3 and 5 and can be stored for long periods, whereas it is comparatively instable at alkaline pH.

Dimethyl sulfoxide (DMSO), acetone, ethyl acetate, ethanol and methanol are used as a solvent for paclitaxel.

One especially preferred embodiment is therefore a catheter balloon of a balloon catheter coated with one layer comprising at least one polyethoxylated castor oil, paclitaxel and shellac. Further the coating of said catheter balloon comprises a top coat or second layer of polyvinyl alcohol-polyethylene glycol graft copolymer. Preferably paxlitaxel and the polyethoxylated castor oil are used in 1.0 weight equivalents to 0.10 to 1.2 weight equivalents.

As a very prosperous active agent for the same purpose of restenosis prophylaxis rapamycin (syn. sirolimus) a hydrophilic macrolid antibiotic appears. This active agent is especially utilized in transplantation medicine as immunosuppressive, wherein contrary to other immunosuppressive active agents rapamycin also inhibits tumour formation. As after transplantation an increased risk of tumor formation exists for the patient the administration of rapamycin is advantageous because other immunosuppressives such as cyclosporin A can even promote tumor formation as is known.

Its chemical structure is as follows:

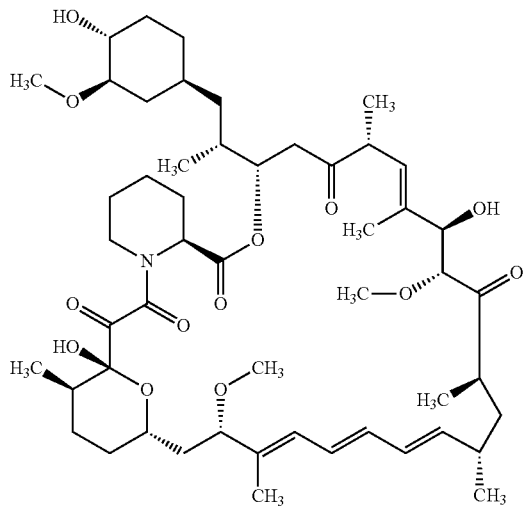 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

IUPAC name:
[3S-[3R*[E(1S*,3S*,4S1],4S*,5R*,8S*,9E,12R",14R*, 15S*,16R*,18S*,19S*,26aR]]-5,6,8,11,12,13,14,15,16,17, 18,19,24,25,26,26a-hexadecahydro-5,19-dihydroxy-3-[2-(4-hydroxy-3-methoxycyclohexyl)-1-methylethenyl]-14, 16-dimethoxy-4,10,12,18-tetramethyl-8-(2-propenyl)-15, 19-epoxy-3H-pyrido[2,1-c][1,4]-oxaazacyclotricosine-1,7, 20,21(4H,23H)-tetron monohydrate.

Rapamycin's mechanism of action is not yet known in detail but it is attributed especially to the complex formation with the protein mTOR (mammalian target of rapamycin) a phosphatidylinositol-3 kinase of 282 kD. As mTOR is responsible for a series of cytokin-mediated signal transduction paths i.a. also for signal paths which are necessary for cell division besides the immunosuppressive effect, rapamycin or sirolimus has also antiphlogistic, antiproliferative and even antimycotic properties.

Proliferation is interrupted in the late G1 phase by stopping the ribosomal protein synthesis. Compared to other antiproliferative active agents rapamycin's mechanism of action can be pointed out as special likewise paclitaxel but which is strongly hydrophobic. Moreover, the immunosuppressive and antiphlogistic effects as described above are more than advantageous because also the extent of inflammatory reactions and of the total immune response as their premature control after stent implantation is decisive for the further success.

Thus, rapamycin has all of the necessary conditions for the utilization against stenoses and restenoses. Rapamycin's limited shelf life on or in an implant is to be mentioned as an additional advantage in comparison to paclitaxel because necessarily the active agent has to be effective in the first decisive weeks after stent implantation. Consequently, the endothelial cell layer which is important for the completion of a healthy healing process can completely grow over the stent and integrate it into the vessel wall.

The same mechanism of action can be found for the known derivatives of rapamycin (biolimus, everolimus, zotarolimus) as the modification is on the molecule's functional groups which are irrelevant for the binding region of mTOR. In different clinical studies (RAVEL, SIRIUS, SIROCCO) rapamycin has shown—contrary to other active agents such as dexamethason, tacrolimus, batimastat—that in comparison to the strongly hydrophobic paclitaxel despite of different physical properties it is more than suitable for combating restenosis.

A further especially preferred embodiment is a catheter balloon coated first (active-agent containing layer) with a mixture of rapamycin and polyethoxylated fatty alcohols, and even more preferred with a mixture of rapamycin and polyethoxylated castor oil, and coated thereafter (top coat or second layer) with polyvinyl alcohol-polyethylene glycol graft copolymer. Preferably rapamycin and polyethoxylated castor oil are used in 1.0 weight equivalents to 0.10 to 1.2 weight equivalents. Alternatively the active agent containing layer may also comprise a further additive, especially shellac.

Coating methods for catheter balloons are disclosed in the international patent application WO 2008/086794 A2. Any kind of common coating process can be used to apply the active agent solution with or without additives like the polyethoxylated compounds and shellac, the top coat and the base coat, respectively, onto the balloon surface such as spray coating, brush coating, dip coating, vapour deposition, pipetting, drop or thread dragging, rolling, electrospinning, plasma deposition, spattering or squirting. Dipping or plasma disposition are preferably used when the whole catheter balloon surface shall be coated. Spattering, brushing and spraying may be preferably used when only a portion of the balloon surface is to be coated. Accordingly, apart from dip coating specific release devices have to be used, comprising nozzles, a plurality of nozzles, a thread, a mesh of threads, a piece of threads, a leather strip, a sponge, a ball, a syringe, a needle, a cannula or a capillary.

The content of the active agent in the active agent containing solution is between 1 µg to 1 mg of the active agent per ml solution, preferably between 10 µg to 500 µg of the active agent per 1 ml solution, more preferably between 30 µg to 300 µg of the active agent per 1 ml solution, and most preferably between 50 µg to 100 µg of the active agent per 1 ml solution.

Preferred is also a total amount of 10 µg to 1000 µg of an active agent per catheter balloon and most preferably 20 µg to 400 µg per catheter balloon.

Generally, an amount of 0.1 µg to 150 µg of active agent, preferably of paclitaxel or rapamycin, per $mm^2$ of the surface of the catheter balloon to be coated can be applied onto the surface of the catheter balloon, while an amount of 0.5 $µg/mm^2$ to 6 $µg/mm^2$ of active agent, preferably of paclitaxel or rapamycin, are preferred and are sufficient in order to achieve the desired effect on restenosis prophylaxis. Preferably the amount of active agent, preferably of paclitaxel or rapamycin, per $mm^2$ balloon surface is between 1.0 $µg/mm^2$ and 15.0 $µg/mm^2$, more preferably between 1.5 $µg/mm^2$ and 10.0 $µg/mm^2$, still more preferably between 2.0 $µg/mm^2$ and 6.0 $µg/mm^2$, and most preferably between 2.5 $µg/mm^2$ and 4 $µg/mm^2$.

An amount of 0.1 µg to 150 µg of the at least one polyethoxylated emulsifier or surfactant per $mm^2$ of the surface of the catheter balloon to be coated can be applied onto the surface of the catheter balloon, while an amount up to 15 $µg/mm^2$ of the at least one polyethoxylated emulsifier or surfactant are sufficient in order to achieve the desired effect efficient transfer of the at least one active agent to the vessel wall tissue. Preferably the amount of the at least one emulsifier or surfactant per $mm^2$ balloon surface is between 1.0 $µg/mm^2$ and 15.0 $µg/mm^2$, more preferably between 1.5

µg/mm² and 10.0 µg/mm², still more preferably between 2.0 µg/mm² and 5.0 µg/mm², and most preferably between 2.5 µg/mm² and 3.5 µg/mm².

An amount of 0.1 µg to 150 µg of polyethylene glycol per mm² of the surface of the catheter balloon to be coated can be applied onto the surface of the catheter balloon, while an amount up to 15 µg/mm² polyethylene glycol are sufficient in order to achieve the desired effect efficient transfer of the at least one active agent to the vessel wall tissue. Preferably the amount of polyethylene glycol per mm² balloon surface is between 1.0 µg/mm² and 15.0 µg/mm², more preferably between 1.5 µg/mm² and 10.0 µg/mm², still more preferably between 2.0 µg/mm² and 5.0 µg/mm², and most preferably between 2.5 µg/mm² and 3.5 µg/mm².

Preferred is a catheter balloon having an active agent containing layer with a proportion of the active agent and the at least one polyethoxylated emulsifier or surfactant from 90% per weight of active agent to 10% per weight of the at least one polyethoxylated emulsifier or surfactant to 10% per weight of active agent to 90% per weight of the at least one polyethoxylated emulsifier or surfactant. Especially preferred is a catheter balloon having an active agent containing layer with a proportion of the active agent and the at least one polyethoxylated emulsifier or surfactant from 65% per weight of active agent to 35% per weight of the at least one polyethoxylated emulsifier or surfactant to 35% per weight of active agent to 65% per weight of the at least one polyethoxylated emulsifier or surfactant. Even more preferred is a catheter balloon having an active agent containing layer with a proportion of the active agent and the at least one polyethoxylated emulsifier or surfactant from 55% per weight of active agent to 45% per weight of the at least one polyethoxylated emulsifier or surfactant to 45% per weight of active agent to 55% per weight of the at least one polyethoxylated emulsifier or surfactant.

The further excipients or carrier substances, like shellac and polyethylene glycol, may be added in a weight ratio of up to 50% per weight relative to the at least one polyethoxylated emulsifier or surfactant used, preferably up to 40% per weight, more preferably up to 30% per weight, more preferably up to 20% per weight and especially preferably up to 10% per weight relative to the used polyethoxylated emulsifier or surfactant.

Also preferred is a catheter balloon with a coating whose molar ratio of active agent to the at least one polyethoxylated emulsifier or surfactant and a possible further additive, like shellac and polyethylene glycol, from 90% active agent to 10% matrix substances (polyethoxylated emulsifier or surfactant and shellac) to 10% of active agent to 90% of matrix substances. Further preferred are mixtures of 1:5 to 5:1 and even more preferably from 1:2 to 2:1.

The afore-mentioned %-values are especially preferred for polyethoxylated castor oil as polyethoxylated emulsifier or surfactant.

An amount of 0.1 µg to 250 µg of top coat per mm² of the surface of the catheter balloon to be coated can be applied onto the active agent coating of the catheter balloon, while an amount up to 20 µg/mm² of the compound forming the top coat are sufficient in order to achieve the desired efficient transfer of the at least one active agent to the vessel wall tissue. Preferably the amount of the compound forming the top coat per mm² balloon surface is between 1.0 µg/mm² and 15.0 µg/mm², more preferably between 1.5 µg/mm² and 10.0 µg/mm², still more preferably between 2.0 µg/mm² and 5.0 µg/mm², and most preferably between 2.5 µg/mm² and 3.5 µg/mm².

An amount of 0.1 µg to 50 µg of a further additive per mm² of the surface of the catheter balloon to be coated can be applied onto the surface of the catheter balloon.

Preferably the amount of the at least one further additive, like shellac, per mm² balloon surface is between 0.2 µg/mm² and 10.0 µg/mm², more preferably between 0.5 µg/mm² and 8.0 µg/mm², still more preferably between 1.0 µg/mm² and 5.0 µg/mm², and most preferably between 1.5 µg/mm² and 3.5 µg/mm².

A stent which is optionally crimped on the catheter balloon can also be coated according to the invention. The same concentrations of the active agents are preferred as for the catheter balloon.

Furthermore, the catheter balloon can be coated in its expanded (inflated) or deflated state. According to the invention, the catheter balloon does not have to be completely coated. Partial coating of the catheter balloon or partial loading of certain texture elements onto the surface of the catheter balloon may be sufficient. A special catheter balloon including micro-needles or micro-pores or micro-chambers is disclosed in the international patent application no. WO 02/043796 A2 issued to Scimed Life Systems, Inc., USA, wherein inflatable and textured areas are present on the balloon surface. In said embodiment, loading or inflating certain portions of the balloon surface would be sufficient to achieve the desired therapeutic success, wherein it is also possible, evidently, that the whole surface is coated.

Briefly, one suitable coating method using a coating device comprises the following steps:

A) providing an uncoated catheter balloon;

B) placing the balloon into a horizontal position or inclined up to a suitable degree;

C) providing a solution of an active agent;

D) providing a solution for a top coat;

E) setting the coating device in position to transfer the solution for the active agent solution and the solution for the top coat onto the surface of the catheter balloon F) applying the respective solution G) drying the coated catheter balloon.

According to the invention the solution of an active agent used in the above described coating methods may also contain at least one polyethoxylated surfactant or at least one polyethoxylated emulsifier and further additives like shellac. Alternatively another solution may be provided comprising the at least one polyethoxylated surfactant or at least one polyethoxylated and optionally shellac. Said solution should be applied to the balloon before the solution containing the active agent is applied.

Hence, according to the invention the coating method can optionally comprises further steps:

C1) providing a solution of at least one polyethoxylated surfactant or at least one polyethoxylated emulsifier and optionally shellac or polyethylene glycol, and E1) applying the solution of the at least one polyethoxylated surfactant or at least one polyethoxylated emulsifier to the catheter balloon.

Step C1) is carried out following step C) and step E1) following step E). For coating by dipping, the catheter balloon is dipped into a container containing the solution for the base coat, the active agent solution or solution for the top coat.

Optionally drying steps can follow the application of each single solution.

Another coating method using a coating device comprises the following steps:

A') providing an uncoated balloon;
B') placing the balloon into a horizontal position or inclined up to a suitable degree;
C') providing a solution for a base coat;
D') providing a solution of an active agent;
E') providing a solution for a top coat;
F') setting the coating device in position to transfer the solution for the base coat, the active agent solution and the solution for the top coat onto the surface of the catheter balloon
G') applying the respective solution
H') drying the coated catheter balloon.

According to the invention the coating method can optionally comprises further steps:

C'1) providing a solution of at least one polyethoxylated surfactant or at least one polyethoxylated emulsifier and optionally shellac or polyethylene glycol, and
F'1) applying the solution of the at least one polyethoxylated surfactant or at least one polyethoxylated emulsifier to the catheter balloon.

Step C'1) is carried out following step C') and step F'1) following step F') in a way that the at least one polyethoxylated surfactant or at least one polyethoxylated emulsifier is integrated into the coating of the catheter balloon above the base layer. Alternatively, the at least one polyethoxylated surfactant or at least one polyethoxylated emulsifier may be mixed with the active agent solution. The topcoat is always free of active agents and the at least one polyethoxylated surfactant or at least one polyethoxylated emulsifier. This means that at least two different coating solutions have to be prepared: one with an active agent and one without for the topcoat or top layer.

For coating by dipping, the catheter balloon is dipped into a container containing the solution for the base coat, the active agent solution or solution for the top coat.

Optionally drying steps can follow the application of each single solution.

It is preferred that step F' is carried out in a way that the solution of the active agent penetrates the base coat.

The drying steps G) and H') can be performed at room temperature or at elevated temperatures up to 50° C. and at atmospheric pressure or under reduced pressure to high vacuum. As mentioned above, the drying steps G) and H') may also be performed after application of each layer, which means a drying step is also possible subsequently after the solution of the active agent has been applied. Thereby the first drying steps are preferably conducted at room temperature and atmospheric pressure, while preferably after the last coating step of the method the drying step is more intensive, i.e. longer or with vacuum or with elevated temperature.

According to the invention the coating methods can optionally further comprise step H or I') respectively:

H) or I') Sterilization of the coated catheter balloons.

The sterilization is preferably performed with ethylene oxide.

Catheter balloons which are coated according to the invention are preferably suited for the treatment and prophylaxis of in-stent restenosis, i.e. a reoccurring vessel constriction within an already implanted stent. In such in-stent restenosis the placement of another stent inside the already existing stent is particularly problematic as the vessel in general can only poorly be widened by the second stent. Herein the application of an active agent by means of balloon dilation offers an ideal treatment method since this treatment can be repeated several times, if necessary, and from a therapeutic point of view may obtain the same or significantly better results than another stent implantation. Furthermore, the catheter balloons coated according to the invention are particularly suited for the treatment of small vessels, preferably those vessels with a vessel diameter less than 2.5 mm, more preferably of less than 2.4 mm, more preferably of less than 2.3 mm, more preferably less than 2.25 mm, and even more preferably of less than 2.2 mm.

The catheter balloons coated according to the invention are preferably one component of a balloon catheter. Therefore one preferred embodiment is a balloon catheter comprising a catheter balloon with a coating comprising at least one active agent and a top coat consisting of a polyvinyl alcohol-polyethylene glycol graft copolymer. Thus the present invention also relates to balloon catheter with a catheter balloon coated according to the present invention. The balloon catheters according to the invention are suitable to prevent or to reduce restenosis.

Apart from in-stent-restenosis, the catheter balloons coated according to the invention can also be preferably used for the prevention, treatment or reduction of stenosis, atherosclerosis and all other forms of occluded vessels.

The catheter balloons coated according to the invention are preferably used in the cardiovascular area, but the catheter balloons coated according to the invention are also suited for the treatment of peripheral blood vessels, vessel constrictions of biliary tracts, esophagus, urinary tracts, pancreas, renal tracts, pulmonary tracts, trachea, small intestine and large intestine.

The following figures and examples illustrate potential embodiments of the invention without limiting the scope of the invention to said precise examples.

The inventors could show in a proof-of-principle study that among the devices tested, the balloon according to the invention comprising paclitaxel, shellac, CREMOPHOR® ELP (polyethoxylated castor oil) and a top coat of PVA-PEG (Group 3) allows for the accumulation of therapeutic active agent concentrations in the arterial wall for at least 5 days, with peak tissue accumulation after 48 hours post deployment. Already one hour after vasodilatation using the balloon according to the invention comprising paclitaxel, shellac, CREMOPHOR® ELP (polyethoxylated castor oil) and a top coat of PVA-PEG the average amount of paclitaxel in the arterial tissue was around 300 ng active agent/mg tissue. Similar results shows Group 2 testing a balloon coating of paclitaxel together with CREMOPHOR® ELP (polyethoxylated castor oil) and a top coat of PVA-PEG. The average amount of paclitaxel in the arterial tissue for Group 4 comprising a balloon coating of paclitaxel together with CREMOPHOR® ELP (polyethoxylated castor oil) and a top coat of PEG after 1 hour were considerably less and even worse were the results of Group 5 using a catheter balloon coating of paclitaxel together with CREMOPHOR® ELP (polyethoxylated castor oil) and a top coat of PVA. Worst results (around 5 and 10 ng active agent/mg tissue) showed study Groups 1 and 6 using a catheter balloon without any top coat. In summary the proof-of-principle study shows that after vasodilatation using a paclitaxel eluting catheter balloon a top coat increases the amount of paclitaxel transferred to and incorporated by the arterial tissue. Further it could be shown that a top cot consisting of a polyvinyl alcohol—polyethylene glycol graft copolymer is more efficient that a top coat of polyvinyl alcohol or polyethylene glycol. Therefore the present invention relates to a catheter balloon coated with at least one active agent and a top coat on said active agent consisting of a polyvinyl alcohol-polyethylene glycol graft copolymer which seems to be to optimal top coat material for a paclitaxel coated catheter balloon.

EXAMPLES

Example 1

Figure 1:
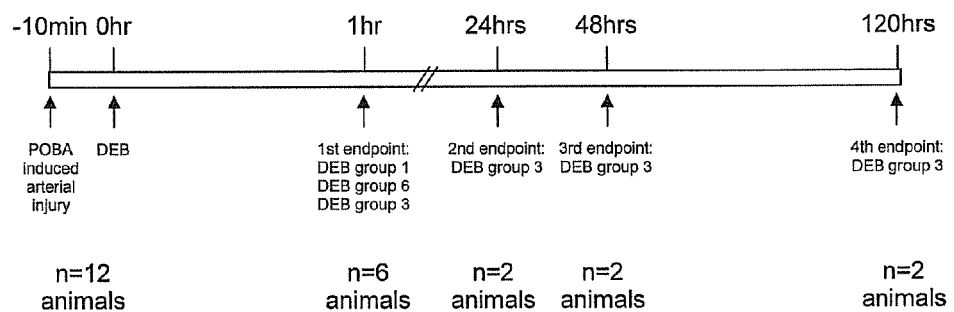
FIG. 1: Study design and experimental procedure of example 6.
Figure 2:
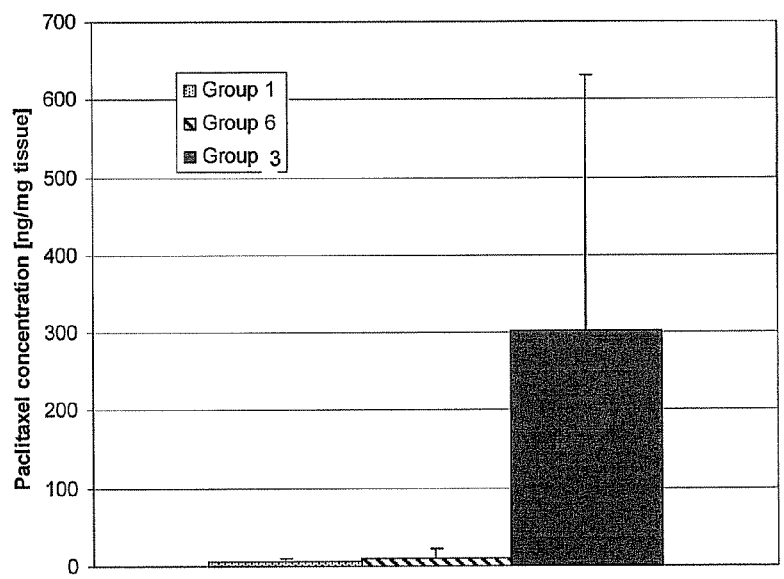
FIG. 2: Mean tissue paclitaxel concentrations of the 3 test DEBs (example 6) one hour after deployment. The mean active agent concentrations were assessed from 4 vessels.
Figure 3:
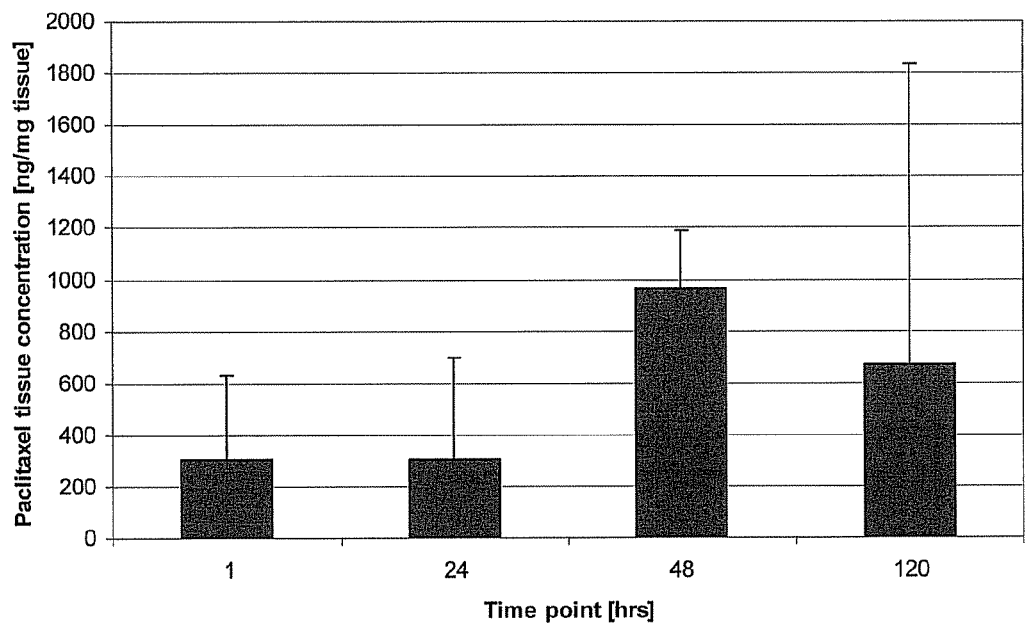
FIG. 3: Time dependent mean tissue active agent concentrations of the Group 3 (example 6). The data are derived from 4 (1, 24 and 48 hours) and 3 (120 hours) treated vessels.
Figure 4:
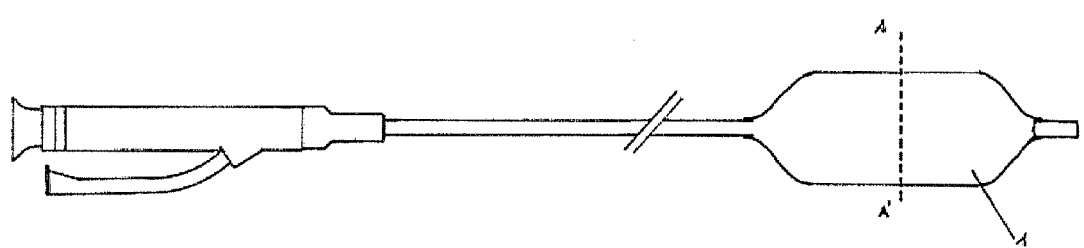
FIG. 4: Depicts a perspective view of one embodiment of a Balloon catheter comprising a catheter balloon according to the present invention.
Figure 5:
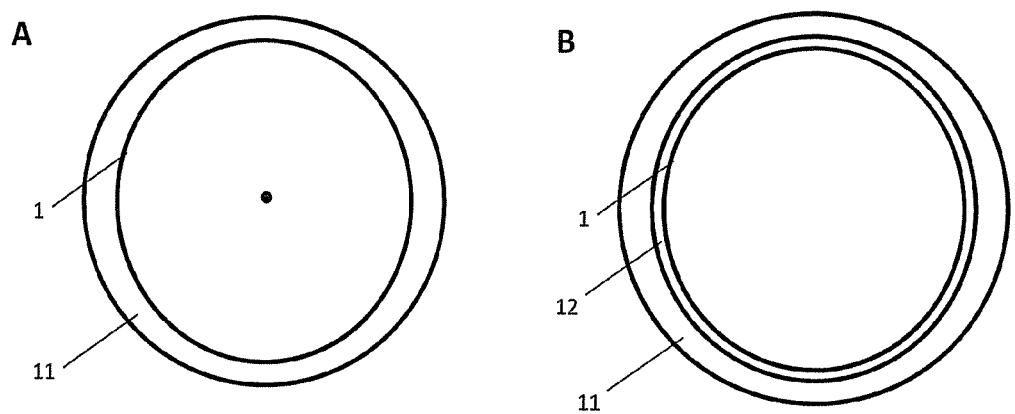
FIG. 5: Depicts a cross-section view of the balloon catheter of FIG. 4 along line A-A' showing A) a catheter balloon (1) with an active agent coating (10) and a top coat of polyvinyl alcohol—polyethylene glycol graft copolymer (11) and B) a catheter balloon (1) with an active agent coating (10) and a top coat of a polyvinyl alcohol—polyethylene glycol graft copolymer (11) and a base coat (12).

A folded catheter balloon is provided which is coated with a solution of polyethoxylated castor oil and paclitaxel in chloroform via the drop drag method so that the final concentration of the active agent is 4.0 µg/mm$^2$ and of the emulsifier 3.0 µg/mm$^2$ of the balloon surface. The catheter balloon is left to dry at room temperature for 1 h. Then a solution of top coat of a polyvinyl alcohol-polyethylene glycol graft copolymer consisting of 75% polyvinyl alcohol units and 25% polyethylene glycol units is applied onto the layer of paclitaxel. The top coating is dried at a temperature of 50° C. at low vacuum.

Example 2

A folded catheter balloon is coated via pipetting. At first a base coat layer of polyvinyl alcohol-polyethylene glycol graft copolymer which is solved in ethanol is applied, followed by an immediate coating with a solution of paclitaxel in ethanol and polyethoxylated fatty alcohols and polyethoxylated castor oil, so that the concentration of paclitaxel is 4.0 µg/mm$^2$ and of the Polyethoxylated fatty alcohols and polyethoxylated castor oil is 3.0 µg/mm$^2$ of the balloon surface. The catheter balloon is left to dry at room temperature for 1 h. Then a solution of top coat of a polyvinyl alcohol-polyethylene glycol graft copolymer consisting of 75% polyvinyl alcohol units and 25% polyethylene glycol units is applied onto the layer of paclitaxel. The top coating is dried at a temperature of 50° C. at low vacuum.

Example 3

A catheter balloon coated in its folds with paclitaxel and polyethoxylated fatty alcohols and polyethoxylated castor oil via the capillary method and having an amount of 2 µg paclitaxel per mm$^2$ and of polyethoxylated fatty alcohols and polyethoxylated castor oil 3.0 µg/mm$^2$ and a top coat of a polyvinyl alcohol-polyethylene glycol graft copolymer consisting of 75% polyvinyl alcohol units and 25% polyethylene glycol applied onto the layer of paclitaxel is provided. Said catheter balloon is folded and a titanium stent is crimped which is coated with a polymeric carrier system polyvinyl alcohol containing the active agent paclitaxel in a preferably cytostatic dosage. The titanium stent was previously coated with a solution of paclitaxel. On the titanium stent there are ca. 2.5 µg paclitaxel per mm$^2$ stent surface.

Example 4

A catheter balloon is preferably coated in a first step with a polyvinyl alcohol, and subsequently coated preferably by the squirting method with a viscous mixture of polyethylene, polyethoxylated fatty alcohols and polyethoxylated castor oil and rapamycin. Then a solution of top coat of a polyvinyl alcohol-polyethylene glycol graft copolymer consisting of 75% polyvinyl alcohol units and 25% polyethylene glycol units. The coating is dried at a temperature of 50° C. at low vacuum.

Example 5: Proof-of-Principle Study for the Effective Active Agent Transfer of 6 Different Paclitaxel-Eluting Balloons (Referred to as DEB) in a Healthy Rabbit Model This study was carried out at the 'Deutsches Herzzentrum München'—clinic at the Technical University Munich. The appropriate approval of regional Bioethical Committee was obtained. HPLC-MS-based analysis for active agent content in tissue was conducted at ic42 Laboratory, University of Colorado, USA.

Six different catheter balloons with the following coatings and carrier matrices were evaluated:

Device 1: paclitaxel-eluting balloon "Group 1", 3.0×20 mm, 3.0 µg/mm$^2$ Paclitaxel, 0.5 µg/mm$^2$ Shellac, 2.5 µg/mm$^2$ Cremophor® ELP (polyethoxylated castor oil) together in one layer Device 2: paclitaxel-eluting balloon "Group 2", 3.0×20 mm, 3.0 µg/mm$^2$ Paclitaxel, 3.0 µg/mm$^2$ Cremophor® ELP (polyethoxylated castor oil) together in one layer and 3.0 µg/mm$^2$ PVA-PEG as a top-coat Device 3: paclitaxel-eluting balloon "Group 3 (referred to as DEB RESTORE)", 3.0×20 mm, 3.0 µg/mm$^2$ Paclitaxel, 0.5 µg/mm$^2$ Shellac, 2.5 µg/mm$^2$ Cremophor® ELP (polyethoxylated castor oil) and 3.0 µg/mm$^2$ PVA-PEG as a top-coat Device 4: paclitaxel-eluting balloon "Group 4", 3.0×20 mm, 3.0 µg/mm$^2$ Paclitaxel, 3.0 µg/mm$^2$ Cremophor® ELP (polyethoxylated castor oil) and 3.0 µg/mm$^2$ PEG (average molecular weight of PEG within the range of 11,000 to 12,000 Daltons) as a top-coat Device 5: paclitaxel-eluting balloon "Group 5", 3.0×20 mm, 3.0 µg/mm$^2$ Paclitaxel, and 3.0 µg/mm$^2$ PVA as a top-coat (average molecular weight of PVA within the range of 30,000 Daltons to 35,000 Daltons)

Device 6: paclitaxel-eluting balloon "Group 6", 3.0×20 mm, 3.0 µg/mm$^2$ Paclitaxel together with 3 µg/mm$^2$ Cremophor® ELP (polyethoxylated castor oil)

Analysis time points of arterial tissue were scheduled at 1 hour, 24 hours, 48 hours and 120 hours.

Study Design:

A total of 47 DEBs were deployed in 24 healthy New Zealand White rabbits (please refer to table 3). For this purpose animals were anaesthetized with propofol and intra surgery analgesia was secured by repetitive boli of fentanyl. Animals were intubated, mechanically ventilated and at all times controlled for vital signs (pulse-oximetry and capnography). Anticoagulation was achieved by administration of 500 IU heparin and 40 mg aspirin i.v. Arterial access was conducted by cut down of the common carotid artery. A swan ganz catheter was advanced over the aortic arch under fluoroscopic guidance just before the bifurcation of the common iliac arteries of the abdominal aorta and an initial angiogram was performed. A guide wire was then placed in the external iliac artery. Wire guided balloon injury (POBA) with single balloon inflation [3.0×10 mm size balloon (Elect®, Biotronik SE & Co. KG) at nominal pressure (7 atm) held for 30 seconds] within the middle portion of the external iliac artery was performed to induce arterial injury and facilitate active agent uptake into the vascular wall of healthy arteries. Afterwards the DEB (3.0×20 mm) was deployed covering the whole length of the induced lesion. The DEBs were inflated at nominal pressure (6 atm) for 60 seconds. Per time point and group, 4 DEBs were bilaterally deployed in the iliac arteries of 2 rabbits utilizing the technique explained above. Five minutes after the procedure, a final angiogram was conducted. To determine DEBs with effective active agent delivery capability to the arterial tissue, all DEB groups were assessed at 1 hour following deployment. The DEB showing the most promising tissue active agent content (Group 3, DEB-RESTORE) was then further analyzed at 24 hours, 48 hours and 120 hours following DEB expansion. Animals with a study in-life phase (time point 48 and 120 hours) received oral anticoagulation once daily the day after surgery with 40 mg aspirin until study termination.

TABLE 1

Scheme of Implantation

| Animal Number | Animal ID | Time Point | Vessel Left iliac artery | Vessel Right iliac artery |
|---|---|---|---|---|
| 1 | 1_12 | 1 hour | Group 1 #2 | Group 1 #1 |
| 2 | 2_12 | 1 hour | Group 1 #3 | Group 1 #4 |
| 3 | 3_12 | 1 hour | Group 3 #1 | Group 3 #2 |
| 4 | 4_12 | 1 hour | Group 3 #4 | Group 3 #3 |
| 5 | 5_12 | 1 hour | Group 6 #2 | Group 6 #1 |
| 6 | 6_12 | 1 hour | Group 6 #3 | Group 6 #4 |
| 13 | 13_12 | 1 hour | Group 2 #2 | Group 2 #1 |
| 14 | 14_12 | 1 hour | Group 2 #4 | Group 2 #3 |
| 15 | 15_12 | 1 hour | Group 4 #1 | Group 4 #2 |
| 16 | 16_12 | 1 hour | Group 4 #3 | Group 4 #4 |
| 17 | 17_12 | 1 hour | Group 5 #2 | Group 5 #1 |
| 18 | 18_12 | 1 hour | Group 5 #3 | Group 5 #4 |
| 7 | 7_12 A | 24 hours | Group 3 #6 | Group 3 #5 |
| 8 | 8_12 A | 24 hours | Group 3 #8 | Group 3 #7 |
| 9 | 9_12 | 48 hours | Group 3 #10 | Group 3 #9 |
| 10 | 10_12 | 48 hours | Group 3 #15 | Group 3 #14 |
| 11 | 11_12 | 120 hours | Group 3 #11 | Group 3 #12 |
| 12 | 12_12 | 120 hours | Group 3 #13 | none |

24 animals were assigned to the study. The first 18 animals were analyzed for arterial tissue active agent content at 1 hour following deployment of all test DEBs. The remaining 6 animals were assigned to the Group 3 and analyzed after 24, 48 and 120 hours. Prior to DEB deployment the external iliac arteries were injured by inflating an angioplasty balloon catheter (Elect©, Biotronik SE & Co. KG, 3.0×10 mm, 7 atm inflation pressure) within the middle portions of the arteries for 30 seconds.

For study termination animals were anaesthetized at the respective time points and shortly after euthanized with pentobarbital overdose i.v. Animals of the 1 hour group remained under anaesthesia until study termination and tissue harvest. Following euthanasia the abdomen was cut open and the abdominal aorta and caudal vena cava were exposed and accessed with arterial sheaths. Consecutively the vessels were flushed with 500 ml heparinized Ringers solution via the arterial sheath until blood clearance. Treated external iliac arteries were then carefully dissected, explanted and snap frozen in liquid nitrogen. Eighteen animals were euthanized 1 hour following DEB deployment including all designated treatment groups (n=4 arteries per group), while the remaining six animals of the Group 3 were euthanized at 24 hours, 48 hours and 5 days following balloon expansion (n=4 arteries for the 24 and 48 hour time point; n=3 arteries for the 120 hour time point). Treated iliac arteries were stored at −70° C. until shipment on dry ice to the analytic laboratory. Explanted treated vessels were weighed, homogenized and the undiluted homogenate was measured for paclitaxel content. At all time points, the batch samples (1st batch=1 hour samples of the test DEBs; 2nd batch=24, 48 and 120 hour samples of the Group 3, DEB-RESTORE) were clearly identified and were processed on the same day using the same extraction method. Samples showing over detection range paclitaxel content were diluted 1:100 and 1:500 and were repeatedly measured.

Results:

All animals survived the procedure without signs of toxicity. There were no adverse effects noted after DEB deployment and the post DEB expansion angiography showed patent vessels and no sign of vessel wall dissection. Macroscopically, at the time of vessel explantation, there were also no signs of vessel trauma or dissection. Of note was that the vessels of the animal 8_12 A (24 hour Group 3) and of the animals 9_12 and 10_12 (both animals of the 48 hour Group 3) showed 1-2 mm long white depositions located at the ventral site of the arteries. This phenomenon was not observed in the 1 hour and 120 hour groups. Animals with an in-life phase of the study (24, 48 and 120 hour Group 3) showed no changes in blood perfusion of the treated legs as assessed clinically by daily palpation of the femoral artery pulse and checking the toes for signs of hypoxia.

HPLC-based analysis of the tissue active agent concentrations revealed that the DEB group 1 exhibited an active agent concentration of 5.19±3.95 ng active agent/mg tissue (n=4 arteries) in the arterial wall 1 hour after DEB deployment. The tissue concentrations ranged from 1 to 10 ng/mg.

The mean tissue active agent concentration analyzed for Group 6 in the arterial wall 1 hour after DEB deployment was 10.72±11.24 ng active agent/mg tissue (n=4 arteries). The tissue concentrations ranged from 4 to 27 ng/mg.

One hour after balloon expansion the Group 3 showed a high amount of active agent within the arterial tissue as represented by a mean paclitaxel concentration of 303.29±326.98 ng active agent/mg tissue (n=4 arteries). Notably, there was a high variability in the arterial wall active agent up-take ranging from 2 to >700 ng/mg tissue. Analysis of arterial active agent concentration at later time points revealed that high concentrations of active agent were still encountered for up to 120 hours (resembling the latest analyzed time point).

24 hours after Group 3 deployment the mean tissue concentration of paclitaxel was 302.65±391.71 ng active agent/mg tissue (n=4 arteries). At 48 hours, a rise in tissue active agent concentration up to a mean value of 961.94±226.54 ng active agent/mg tissue was denoted within the 4 analyzed vessels. At the latest analyzed time point of 120 hours, there was a slight decrease in mean active agent concentration (674.26±1158.78 ng active agent/ mg tissue). Yet there was a strong variability of tissue active agent concentrations between the treated vessels ranging from 4 to >2000 ng/mg (n=3 arteries).

TABLE 2

Mean active agent tissue concentrations (ng active agent/mg tissue)

| Time point | Device Grouping | | |
|---|---|---|---|
| | Group 1 | Group 6 | Group 3 |
| 1 hour (n = 4) | 5.19 ± 3.95 | 10.72 ± 11.24 | 303.29 ± 326.98 |
| 24 hours (n = 4) | Not performed | Not performed | 302.65 ± 391.71 |
| 48 hours (n = 4) | Not performed | Not performed | 961.94 ± 226.54 |
| 120 hours (n = 4) | Not performed | Not performed | 674.26 ± 1158.978 |

The observed divergences in active agent up-take were within the expected range when utilizing healthy animal models, as active agent up-take in healthy vessels is primarily dependent on the degree of tissue injury prior to DEB deployment. In one case (Group 3, Balloon number 5, 24 hour time point) the denoted low active agent up-take can be explained by loss of the paclitaxel coating during extraction of the protective sheath.

Among the test devices the Group 3 achieved significant paclitaxel concentrations that were previously shown to be effective in neointimal growth reduction among contemporary drug eluting balloon devices (Unverdorben et al, Circ 2009; Joner et al, Thromb Haemost 2011).

As a consequence the Group 3 was further analyzed for its pharmacokinetic profile up to 120 hours (5 days) following deployment. The application of this device appears to be safe as there was no evidence for vessel wall dissections or aneurysms at follow-up for up to 5 days and animals also showed no signs of malperfusion of the treated legs suggesting absence of embolization. According to the findings of the current study, there was a rapid active agent up-take of paclitaxel within the arterial tissue within the first 24 hours. Of note was that tissue concentrations further increased within 24 and 48 hours following DEB-RE-STORE deployment which provides evidence for the delayed active agent up-take capacity of the Group 3 when deployed in healthy arteries. This is recognized as a favorable effect of contemporary drug eluting balloons, as the prolonged bioavailability within the vessel wall is a hallmark of enhanced antiproliferative potential.

CONCLUSION

This proof-of-principle study showed that among the devices tested, the balloon according to the invention comprising a top coat (Group 3) allows for the accumulation of therapeutic active agent concentrations in the arterial wall for at least 5 days, with peak tissue accumulation after 48 hours post deployment.

The invention claimed is:
1. A catheter balloon with a coating comprising at least one active agent and a top coat consisting of a polyvinyl alcohol-polyethylene glycol graft copolymer, wherein the at least one active agent is incorporated in a matrix of at least one polyethoxylated surfactant together with shellac or at least one polyethoxylated emulsifier together with shellac and wherein the molar ratio of the active agent to the at least one polyethoxylated emulsifier together with shellac or to the at least one polyethoxylated surfactant together with shellac is in the range from 1:2 to 2:1, wherein the coating further comprises a base coat on the catheter balloon consisting of shellac.

2. A catheter balloon according to claim 1, wherein the polyvinyl alcohol—polyethylene glycol graft copolymer consists of 75% polyvinyl alcohol units and 25% polyethylene glycol units.

3. A catheter balloon according to claim 1, wherein the at least one polyethoxylated surfactant or at least one polyethoxylated emulsifier is selected from the group consisting of:
polyethoxylated alcohols, polyethoxylated oils, polyethoxylated castor oil, polyethoxylated glycerol, polyethoxylated fatty acid esters, polyethoxylated phenols, polyethoxylated amines, and polyethoxylated fatty alcohols.

4. A catheter balloon according to claim 1 wherein the at least one polyethoxylated surfactant or at least one polyethoxylated emulsifier is a polyethoxylated castor oil.

5. A catheter balloon according to claim 4, wherein the at least one polyethoxylated surfactant or at least one polyethoxylated emulsifier is a polyethoxylated surfactant or at least one polyethoxylated emulsifier purified by removing potassium ions and free fatty acids.

6. A catheter balloon according to claim 1, wherein the at least one polyethoxylated surfactant or at least one polyethoxylated emulsifier is a polyethoxylated surfactant or at least one polyethoxylated emulsifier prepared by reacting castor oil with ethylene oxide in a molar ratio of 1:35.

7. A catheter balloon according to claim 1, wherein the at least one active agent is an antiproliferative, immunosuppressive, anti-angiogenic, anti-inflammatory, anti-restenotic, or anti-thrombotic agent.

8. A catheter balloon according to claim 7, wherein the at least one antiproliferative, immunosuppressive, anti-angiogenic, anti-inflammatory, anti-restenotic, and/or anti-thrombotic agent is selected from the group consisting of:
abciximab, acemetacin, acetylvismione B, aclarubicin, ademetionine, adriamycin, aescin, afromosone, akagerine, aldesleukin, amidorone, aminoglutethimide, amsacrine, anakinra, anastrozole, anemonin, anopterine, antimycotics antithrombotics, apocymarin, argatroban, aristolactam-All, aristolochic acid, ascomycin, asparaginase, aspirin, atorvastatin, auranofin, azathioprine, azithromycin, baccatin, bafilomycin, basiliximab, bendamustine, benzocaine, berberine, betulin, betulinic acid, bilobol, bisparthenolidine, bleomycin, combrestatin, Boswellic acids and derivatives thereof, bruceanol A, B and C, bryophyllin A, busulfan, antithrombin, bivalirudin, cadherins, camptothecin, capecitabine, o-carbamoyl-phenoxyacetic acid, carboplatin, carmustine, celecoxib, cepharanthin, cerivastatin, CETP inhibitors, chlorambucil, chloroquine phosphate, cicutoxin, ciprofloxacin, cisplatin, cladribine, clarithromycin, colchicine, concanamycin, coumadin, C-type natriuretic peptide (CNP), cudraisoflavone A, curcumin, cyclophosphamide, ciclosporin A, cytarabine, dacarbazine, daclizumab, dactinomycin, dapsone, daunorubicin, diclofenac, 1,11-dimethoxycanthin-6-one, docetaxel, doxorubicin, daunamycin, epirubicin, erythromycin, estramustine, etoposide, filgrastim, fluroblastin, fluvastatin, fludarabine, fludarabine-5'-dihydrogen phosphate, fluorouracil, folimycin, fosfestrol, gemcitabine, ghalakinoside, ginkgol, ginkgolic acid, glycoside 1a, 4-hydroxyoxycyclo phosphamide, idarubicin, ifosfamide, josamycin, lapachol, lomustine, lovastatin, melphalan, midecamycin, mitoxantrone, nimustine, pitavastatin, pravastatin, procarbazine, mitomycin, methotrexate, mercaptopurine, thioguanine, oxaliplatin, irinotecan, topotecan, hydroxycarbamide, miltefosine, pentostatin, pegaspargase, exemestane, letrozole, formestane, mycophenolate mofetil, β-lapachone, podophyllotoxin, podophyllic acid-2-ethyl hydrazide, molgramostim (rhuGM-CSF), peginterferon α-2b, lenograstim (r-HuG-CSF), macrogol, selectin (cytokine antagonist), cytokinin inhibitors, COX-2 inhibitor, angiopeptin, monoclonal antibodies inhibiting muscle cell proliferation, bFGF antagonists, probucol, prostaglandins, 1-hydroxy-11-methoxycanthin-6-one, scopoletin, NO donors, pentaerythrityl tetranitrate and sydnoimines, S-nitroso derivatives, tamoxifen, staurosporine, β-estradiol, α-estradiol, estriol, estrone, ethinyl estradiol, medroxyprogesterone, estradiol cypionates, estradiol benzoates, tranilast, kamebakaurin and other terpenoids used in cancer therapy, verapamil, tyrosine kinase inhibitors (tyrphostins), paclitaxel and derivatives thereof, 6-α-hydroxy-paclitaxel, taxoteres, mofebutazone, lonazolac, lidocaine, ketoprofen, mefenamic acid, piroxicam, meloxicam, penicillamine, hydroxychloroquine, sodium aurothiomalate, oxaceprol, β-sitosterol, myrtecaine, polidocanol, nonivamide, levomenthol, ellipticine, D-24851 (Calbiochem), colcemid, cytochalasin A-E, indanocine, nocodazole, bacitracin, vitronectin receptor antagonists, azelastine, guanidyl cyclase stimulator, tissue inhibitor of metal proteinase-1 and -2, free nucleic acids, nucleic acids incorporated into virus transmitters, DNA and RNA fragments, plasminogen activator inhibitor 1, plasminogen activator inhibitor 2, antisense oligonucleotides, VEGF inhibitors, IGF-1, active agents from the group of antibiotics, cefadroxil, cefazolin, cefaclor, cefoxitin, tobramycin, gentamicin, penicillins, dicloxacillin, oxacillin, sulfonamides, metronidazole, enoxaparin, heparin, hirudin, PPACK, protamine, prourokinase, streptokinase, warfarin, urokinase, vasodilators, dipyramidole, trapidil, nitroprussides, PDGF antagonists, triazolopyrimidine, seramin, ACE inhibitors, captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators, halofuginone, nifedipine, tocopherol, tranilast, molsidomine, tea polyphenols, epicatechin gallate, epigallocatechin gallate, leflunomide, etanercept, sulfasalazine, tetracycline, triamcinolone, mutamycin, procainimide, retinoic acid, quinidine, disopyrimide, flecainide, propafenone, sotalol, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS), fenoprofen, ibuprofen, indomethacin, naproxen, phenylbutazone, antiviral agents, acyclovir, ganciclovir zidovudine, clotrimazole, flucytosine, griseofulvin, ketoconazole, miconazole, nystatin, terbinafine, antiprotozoal agents, chloroquine, mefloquine, quinine, natural terpenoids, hippocaesculin, barringtogenol-C21-angelate, 14-dehydroagrostistachin, agroskerin, agrostistachin, 17-hydroxyagrostistachin, ovatodiolids, 4,7-oxycycloanisomelic acid baccharinoids B1, B2, B3 and B7, tubeimoside, bruceantinoside C, yadanziosides N and P, isodeoxyelephantopin, tomenphantopin A and B, coronarin A, B C and D, ursolic acid, hyptatic acid A, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, cymarin, hydroxyanopterine, protoanemonin, cheliburin chloride, sinococuline A and B, dihydronitidine, nitidine chloride, 12-p-hydroxypregnadien-3,20-dione, helenalin, indicine, indicine-N-oxide, lasiocarpine, inotodiol, podophyllotoxin, justicidin A and B, larreatin, malloterin, mallotochromanol, isobutyrylmallotochromanol, marchantin A, maytansin, lycoridicin, margetine, pancratistatin, liriodenine, oxoushinsunine, periplocoside A, deoxypsorospermin, psychorubin, ricin A, sanguinarine, manwu wheat acid, methylsorbifolin, chromones of spathelia, stizophyllin, dihydrousambaraensine, hydroxyusambarine, strychnopentamine, strychnophylline, usambarine, usambarensine, liriodenine, daphnoretin, lariciresinol, methoxylariciresinol, syringaresinol, sirolimus (rapamycin), rapamycin derivatives, biolimus A9, pimecrolimus, everolimus, myolimus, novolimus, ridaforolimus, temsirolimus, zotarolimus, tacrolimus, fasudil, epothilones, somatostatin, roxithromycin, troleandomycin, simvastatin, rosuvastatin, vinblastine, vincristine, vindesine, teniposide, vinorelbine, trofosfamide, treosulfan, temozolomide, thiotepa, tretinoin, spiramycin, umbelliferone, desacetylvismione A, vismione A and B, zeorin.

9. A catheter balloon according to claim 8, wherein the at least one active agent is selected from the group consisting of:
paclitaxel and paclitaxel derivatives, taxanes, docetaxel, sirolimus, sirolimus derivatives, biolimus A9, pimecrolimus, everolimus, myolimus, novolimus, ridaforolimus, temsirolimus, zotarolimus, tacrolimus, fasudil and epothilones.

10. A balloon catheter comprising a catheter balloon according to claim 1.

11. The balloon catheter according to claim 10 suitable to prevent or to reduce restenosis.

* * * * *